(12) United States Patent
Aggarwal

(10) Patent No.: US 7,196,105 B2
(45) Date of Patent: Mar. 27, 2007

(54) TREATMENT OF HUMAN MULTIPLE MYELOMA BY CURCUMIN

(75) Inventor: Bharat Aggarwal, Houston, TX (US)

(73) Assignee: Research Development Foundation, Carson City, NV (US)

(*) Notice: Subject to any disclaimer, the term of this patent is extended or adjusted under 35 U.S.C. 154(b) by 408 days.

(21) Appl. No.: 10/602,303

(22) Filed: Jun. 24, 2003

(65) Prior Publication Data

US 2004/0058021 A1 Mar. 25, 2004

Related U.S. Application Data

(60) Provisional application No. 60/390,926, filed on Jun. 24, 2002, now abandoned.

(51) Int. Cl.
*A01N 43/40* (2006.01)
*A61K 31/44* (2006.01)

(52) U.S. Cl. ........................... 514/348; 514/679

(58) Field of Classification Search .......... 514/348, 514/679
See application file for complete search history.

(56) References Cited

U.S. PATENT DOCUMENTS

| | | | |
|---|---|---|---|
| 5,891,924 A | 4/1999 | Aggarwal | 514/679 |
| 2001/0025034 A1 | 9/2001 | Arbiser | 514/114 |
| 2002/0019382 A1 | 2/2002 | Snyder et al. | 514/210.2 |
| 2002/0035090 A1 | 3/2002 | Zeldis | 514/58 |
| 2004/0002499 A1 | 1/2004 | Aggarwal | 514/251 |
| 2005/0049299 A1 | 3/2005 | Aggarwal | 514/456 |

OTHER PUBLICATIONS

CAPLUS DN 51:68566, Ramprasad, C et al, J. Sci. Ind. Res. 1956, 15C, 262-5, abstract.*
www.foodproductdesign.com, Spice Rack, Tumeric Tales, 2001, 1-3.*
Bharti et al, Blood, Feb. 2003, 101 (3), 1053-1062.*
Brennan et al., "Inhibition of nuclear factor kappaB by direct modification in whole cells—mechanism of action of noridihydroguaiaretic acid, curcumin and thiol modifiers," *Biochem. Pharmacol.*, 55:965-973, 1998.
Cheng et al., "Phase I chemoprevention clinical trail of curcumin,," *Proc. Am. Soc. Clin. Oncol.* 17:558a, 1998.
Estrov et al., "Phenylarsine oxide blocks interleukin-1beta-induced activation of the nuclear transcription factor NF-kappaB, inhibits proliferation, and induces apoptosis of acute myelogenous leukemia cells," *Blood*, 94:2844-2853, 1999.

Feinman et al., "Role of NF-kappaB in the rescue of multiple myeloma cells from glucocorticoid-induced apoptosis by bcl-2," *Blood*, 93:3044-3052, 1999.
Giri and Aggarwal, "Constitutive activation of NF-kappaB causes resistance to apoptosis in human cutaneous T cell lymphoma HuT-78 cells. Autocrine role of tumor necrosis factor and reactive oxygen intermediates," *J. Biol. Chem.*, 273:14008-14014, 1998.
Han et al., "Curcumin causes the growth arrest and apoptosis of B cell lymphoma by downregulation of egr-1, c-myc, bcl-XL, NF-kappa B, and p53," *Clin. Immunol.*, 93:152-161, 1999.
Hour et al., "Curcumin enhances cytotoxicity of chemotherapeutic agents in prostate cancer cells by inducing p21(WAF1/CIP1) and C/EBPbeta expressions and suppressing NF-kappaB activation," Prostate, 51:211-218, 2002.
Huang et al., "Effect of dietary curcumin and dibenzoylmethane on formation of 7,12-dimethylbenz[a]anthracene-induced mammary tumors and lymphomas/leukemias in Sencar mice," *Carcingenesis*, 19:1697-1700, 1998.
Ichiki et al., "Regulation of activator protein-1 activity in the mediastinal lymph node metastasis of lung cancer," *Clin. Exp. Metastasis*, 18:539-545, 2001.
Inano et al., "Chemoprevention by curcumin during the promotion stage of tumorigenesis of mammary gland in rats irradiated with gamma-rays," *Carcingenesis*, 20:1011-1018, 1999.
Jaffe et al., "Adjuvant methotrexate and citrovorum-factor treatment of osteogenic sarcoma," N. Engl. J. Med., 291:994-997, 1974.

(Continued)

*Primary Examiner*—Christopher S. F. Low
*Assistant Examiner*—Amy Lewis
(74) *Attorney, Agent, or Firm*—Fulbright & Jaworski L.L.P.

(57) ABSTRACT

All multiple myeloma cell lines examined showed constitutively active IκB kinase (IKK), IκBα phosphorylation and constitutively active NF-κB. Curcumin, a chemopreventive agent, suppressed constitutive IκBα phosphorylation through inhibition of IKK activity and downregulated NF-κB. Curcumin also downregulated expression of NF-κB-regulated gene products such as IκBα, Bcl-2, Bcl-$x_L$, cyclin D1 and interleukin-6. Consequently, curcumin suppressed multiple myeloma cell proliferation and arrested cells at the G1/S phase of the cell cycle. Curcumin also induced apoptosis and chemosensitivity to vincristine. Overall, results presented herein provide a molecular basis for the treatment of multiple myeloma patients with this pharmacologically safe agent.

13 Claims, 29 Drawing Sheets

OTHER PUBLICATIONS

Jang et al., "A curcuminoid and sesquiterpenes as inhibitors of macrophage TNF-alpha release from Curcuma zedoaria," *Planta Med.* 67:550-552, 2001.

Jaruga et al., "Apoptosis-like, reversible changes in plasma membrane asymmetry and permeability, and transient modifications in mitochondrial membrane potential induced by curcumin in rat thymocytes," *FEBS Lett.*, 433(3):287-293, 1998.

Jobin et al., "Curcumin blocks cytokine-mediated NF-kappa B activation and proinflammatory gene expression by inhibiting inhibitory factor I-kappa B kinase activity," *J. Immunol.*, 163:3474-3483, 1999.

Kawamori et al., "Chemopreventive effect of curcumin, a naturally occurring anti-inflammatory agent, during the promotion/progression stages of colon cancer," *Cancer Res.* 59:597-601, 1999.

Kumar et al., "Curcumin (Diferuloylmethane) inhibition of tumor necrosis factor (TNF)-mediated adhesion of monocytes to endothelial cells by suppression of cell surface expression of adhesion molecules and of nuclear factor-kappaB activation," *Biochem. Pharmacol.*, 55:775-783, 1998.

Mehta et al., "Antiproliferative effect of curcumin (diferuloylmethane) against human breast tumor cell lines," *Anti-Cancer Drugs*, 8:470-481, 1997.

Menon et al, "Anti-metastatic activity of curcumin and catechin," *Cancer Lett.*, 141:159-165, 1999.

Mohan et al., "Curcuminoids inhibit the angiogenic response stimulated by fibroblast growth factor-2, including expression of matrix metalloproteinase gelatinase B," *J. Biol. Chem*, 275:10405-10412,2000.

Navis et al., "Dietary curcumin with cisplatin administration modulates tumour marker indices in experimental fibrosarcoma," *Pharmacol. Res.*, 39:175-179, 1999.

Ni et al., "Analysis of expression of nuclear factor kappa B (NF-kappa B) in multiple myeloma: downregulation of NF-kappa B induces apoptosis," *Br. J. Haematol.* 115:279-286, 2001.

Pahl et al., "Activators and target genes of Rel/NF-kappaB transcription factors," *Oncogene*, 18:6853-6866, 1999.

Pan et al., "Comparative studies on the suppression of nitric oxide synthase by curcumin and its hydrogenated metabolites through down-regulation of IkappaB kinase and NFkappaB activation in macrophages," *Biochem. Pharmacol.*, 60:1665-1676, 2000.

Plummer et al., "Inhibition of cyclo-oxygenase 2 expression in colon cells by the chemopreventive agent curcumin involves inhibition of NF-kappaB activation via the NIK/IKK signalling complex," *Oncogene*, 18:6013-6020, 1999.

Podar et al., "Essential role of caveolae in interleukin-6- and insulin-like growth factor I-triggered Akt-1 mediated survival of multiple myeloma cells," *J. Biol. Chem.*, 278(8):5794-801, 2002.

Ramachandran et al., "Differential sensitivity of human mammary epithelial and breast carcinoma cell lines to curcumin," *Breast Cancer Res. and Treat.*, 54:269-278, 1999.

Rao et al., "Chemoprevention of colon carcinogenesis by dietary curcumin, a naturally occurring plant phenolic compound," *Cancer Res.*, 55:259-266, 1995.

Shishodia and Aggarwal, "Nuclear factor-B activation: a question of life and death," *J. Biochem Mol. Biol.*, 35:28-40, 2002.

Simon et al., "Inhibitory effect of curcuminoids on MCF-7 cell proliferation and structure-activity relationships," *Cancer Lett.*, 129:111-116, 1998.

Singh and Aggarwal, "Activation of transcription factor NF-kappa B is suppressed by curcumin (diferuloylmethane)" *J. Biol. Chem.*, 270:24995-25000, 1995.

Singletary et al., "Inhibition of 7,12-dimethylbenz[a]anthracene (DMBA)-induced mammary tumorigenesis and DMBA-DNA adduct formation by curcumin," *Cancer Lett.*, 103:137-141, 1996.

Sonneveld et al., "Cyclosporin A combined with vincristine, doxorubicin and dexamethasone (VAD) compared with VAD alone in patients with advanced refractory multiple myeloma: an EORTC-HOVON randomized phase III study (06914)," *Br. J. Haematol.*, 115(4):895-902.

Westerheide et al., "The putative oncoprotein Bcl-3 induces cyclin D1 to stimulate G(1) transition" *Mol. Cell. Biol.* 21:8428-8436, 2001.

Zhang et al., Zhongguo Yaolixue Tongbao, 17(6):702-704, 2001 (Abstract).

Zhang et al., "Curcumin inhibits cyclooxygenase-2 transcription in bile acid- adn phorbol ester-treated human gastrointestinal epithelial cells," *Carcinogenesis*, 20:445-451, 1999.

Zhang et al., "Tyrosine kinase inhibitor emodin suppresses growth of HER-2/neu-overexpressing breast cancer cells in athymic mice and sensitizes these cells to the inhibitory effect of paclitaxel," *Clin. Cancer Res.*, 5:343-353, 1999.

* cited by examiner

Control      Curcumin-treated

U26

RPMI 8226

Procaspase-9

Procaspase-7

PARP

Untreated

Anti-p65                        Hoechst

NBD-treated

NF-κB (p65)

Patient #20

None

Curcumin

Dexamethason

STAT3

Patient #20

None

Curcumin

Dexamethason

TREATMENT OF HUMAN MULTIPLE MYELOMA BY CURCUMIN

CROSS-REFERENCE TO RELATED APPLICATION

This non-provisional application claims benefit of provisional application U.S. Ser. No. 60/390,926, filed Jun. 24, 2002, now abandoned.

BACKGROUND OF THE INVENTION

1. Field of the Invention

The present invention relates generally to the field of cancer biology. More specifically, the present invention discloses methods of treating human multiple myeloma by curcumin.

2. Description of the Related Art

Multiple myeloma is a B cell malignancy characterized by the latent accumulation in bone marrow of secretory plasma cells with a low proliferative index and an extended life span. Multiple myeloma accounts for 1% of all cancers and >10% of all hematologic cancers. Standard treatment regimen includes a combination of vincristine, BCNU, melphalan, cyclophosphamide, Adriamycin, and prednisone or dexamethasone. Despite treatment with large doses of glucocorticoids and alkylating agents, this malignancy remains incurable. Complete remission rate is 5% and median survival is 30–36 months. In more than 90% of the patients, the disease becomes chemoresistant. Therefore, safe and efficacious agents are urgently needed for treatment of multiple myeloma.

Dysregulation of apoptotic mechanisms in plasma cells is considered a major underlying factor in the pathogenesis and subsequent chemoresistance in multiple myeloma. It is established that IL-6, produced in either an autocrine or paracrine manner, has an essential role in the malignant progression of multiple myeloma by regulating the growth and survival of tumor cells. The presence of IL-6 leads to constitutive activation of Stat 3 which in turn results in expression of high levels of anti-apoptotic protein Bcl-$x_L$. Bcl-2 overexpression, another important characteristic of the majority of multiple myeloma cell lines, rescues these tumor cells from glucocorticoid-induced apoptosis. Treatment of multiple myeloma cells with TNF activates NF-κB, induces secretion of IL-6, induces expression of various adhesion molecules and promotes proliferation. Furthermore, multiple myeloma cells have been shown to express the ligand for the receptor that activates NF-κB (RANKL), a member of the TNF superfamily which could mediate multiple myeloma-induced osteolytic bone disease.

One of the potential mechanisms by which multiple myeloma cells could develop resistance to apoptosis is through the activation of nuclear transcription factor NF-κB. Under normal conditions, NF-κB is present in the cytoplasm as an inactive heterotrimer consisting of p50, p65, and IκBα subunits. Upon activation, IκBα undergoes phosphorylation and ubiquitination-dependent degradation by the 26S proteosome, thus exposing nuclear localization signals on the p50–p65 heterodimer, leading to nuclear translocation and binding to a specific consensus DNA sequence (5'-GGGACTTTC-3', SEQ ID NO. 1). NF-κB binding to DNA activates gene expression that in turn results in gene transcription. Phosphorylation of IκBα occurs through the activation of IκB kinase (IKK). The IκB kinase complex consists of three proteins IKKa, IKKb and IKKg/NF-kB essential modulator (NEMO). IKKα and IKKβ are the kinases that are capable of phosphorylating IκBα, whereas IKKγ/NEMO is a scaffold protein that is critical for IKKα and IKKβ activity.

Extensive research during the past few years has indicated NF-κB regulates the expression of various genes that play critical roles in apoptosis, tumorigenesis, and inflammation. Some of the NF-κB-regulated genes include IκBα, cyclin D1, Bcl-2, bcl-$x_L$, COX-2, IL-6, and adhesion molecules ICAM-1, VCAM-1, and ELAM-1. Recently it was reported that NF-κB is constitutively active in multiple myeloma cells, leading to bcl-2 expression that rescues these cells from glucocorticoid-induced apoptosis. Since multiple myeloma cells express IL-6, various adhesion molecules, Bcl-$x_L$, and Bcl-2 which are all regulated by NF-κB, and since their suppression can lead to apoptosis, it is proposed that NF-κB is an important target for multiple myeloma treatment. However, the prior art is deficient in identifying a pharmacologically safe and effective agent with which to block constitutive NF-κB in multiple myeloma. The present invention fulfills this long-standing need in the art.

SUMMARY OF THE INVENTION

Because of the central role of nuclear transcription factor NF-κB in cell survival and proliferation, the possibility of using it as a target for multiple myeloma treatment was explored by using curcumin (diferuloylmethane), an agent known to have very little or no toxicity in humans. NF-κB was constitutively active in all human multiple myeloma cell lines examined and that curcumin, a chemopreventive agent, downregulated NF-κB in all cell lines as indicated by electrophoretic mobility gel shift assay and prevented nuclear retention of p65 as shown by immunocytochemistry. All multiple myeloma cell lines showed constitutively active IκB kinase (IKK) and IκBα phosphorylation. Curcumin suppressed constitutive IκBα phosphorylation through inhibition of IkB kinase activity. Curcumin also downregulated expression of NF-κB-regulated gene products including IκBα, Bcl-2, Bcl-$x_L$, cyclin D1 and interleukin-6. This led to suppression of proliferation and arrest of cells at the G1/S phase of the cell cycle.

Suppression of NF-κB complex by IKKg/NF-kB essential modulator-binding domain peptide also suppressed proliferation of multiple myeloma cells. Curcumin also induced apoptosis as indicated by activation of caspase-7 and caspase-9 and by PARP cleavage. Curcumin-induced downregulation of NF-κB, a factor that has been implicated in chemoresistance, also induced chemosensitivity to vincristine. These results indicate that curcumin downregulates NF-κB in human multiple myeloma cells, leading to suppression of proliferation and induction of apoptosis.

The present invention also assayed CD138[+] cells from the bone marrow of 22 multiple myeloma patients and checked for activated form of NF-κB and STAT3 by immunocytochemistry. It was found that multiple myeloma cells from all the patients expressed the activated forms of NF-κB and STAT3. Constitutive activation of NF-κB was independently confirmed by electrophoretic mobility gel shift assay. In contrast to multiple myeloma patients, NF-κB and STAT3 were absent in cells from healthy individuals. Suppression of the activation of NF-κB and STAT3 in multiple myeloma cells by ex vivo treatment with curcumin (diferuloylmethane) resulted in a decrease in the viability of cells. Dexamethasone partially suppressed NF-κB activation and was minimally cytotoxic to myeloma cells. Overall, these results indicate that fresh cells from multiple myeloma patients express constitutively active NF-κB and STAT3, and suppression of these transcription factors inhibits the survival of these cells.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1 shows curcumin inhibits constitutive nuclear NF-kB in multiple myeloma.

FIG. 3 shows that curcumin inhibits IκBα phosphorylation and IκB kinase. Five million U266 cells/2.5 ml were treated with curcumin (50 μM) for the indicated times and cytoplasmic extracts were prepared.

FIG. 6 shows that curcumin inhibits the growth of human multiple myeloma cells and induces apoptosis.

FIG. 8 shows that the NEMO-binding domain (NBD) peptide inhibits constitutive NF-κB and induces cytotoxicity in multiple myeloma cells.

DETAILED DESCRIPTION OF THE INVENTION

Figure 1A:
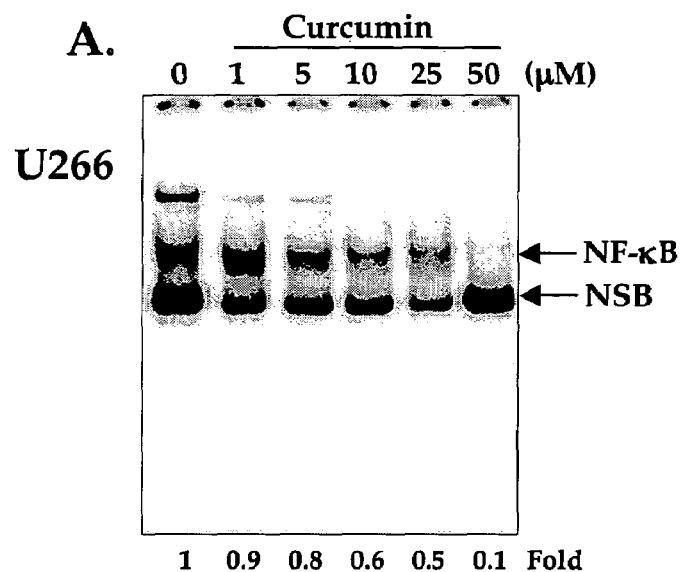
FIG. 1A: Dose response of NF-κB to curcumin treatment of U266 cells. Two million cells/ml were treated with the indicated concentrations of curcumin for 4 h and tested for nuclear NF-kB by EMSA.
Figure 1B:
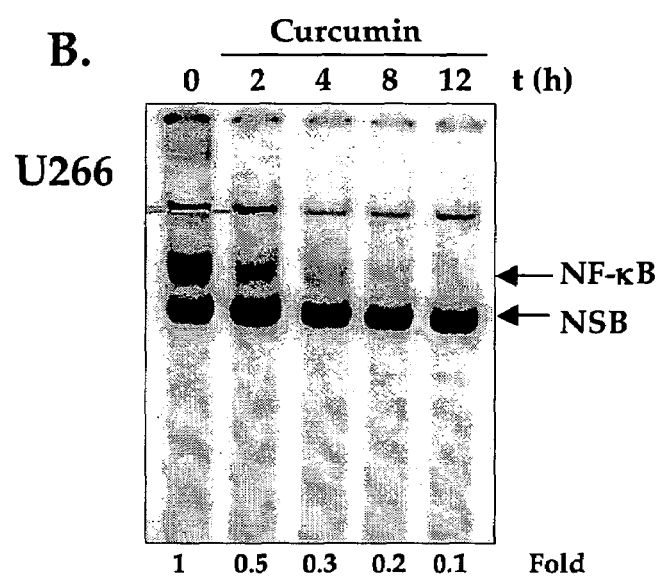
FIG. 1B: Effect of exposure duration on curcumin-induced NF-κB suppression in U266 cells. Cells were treated with curcumin (50 μM) for the indicated times and tested for nuclear NF-kB by EMSA.
Figure 1C:
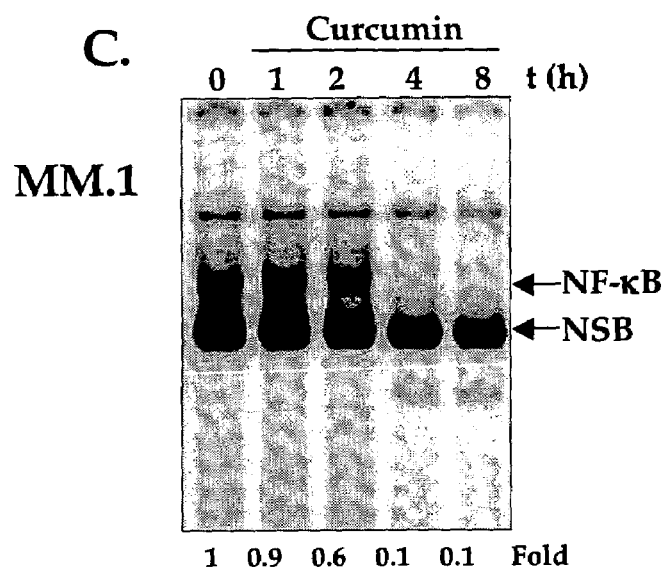
FIG. 1C: Effect of exposure duration on curcumin-induced NF-κB suppression in MM.1 cells. Cells were treated as described in FIG. 1B.
Figure 1D:
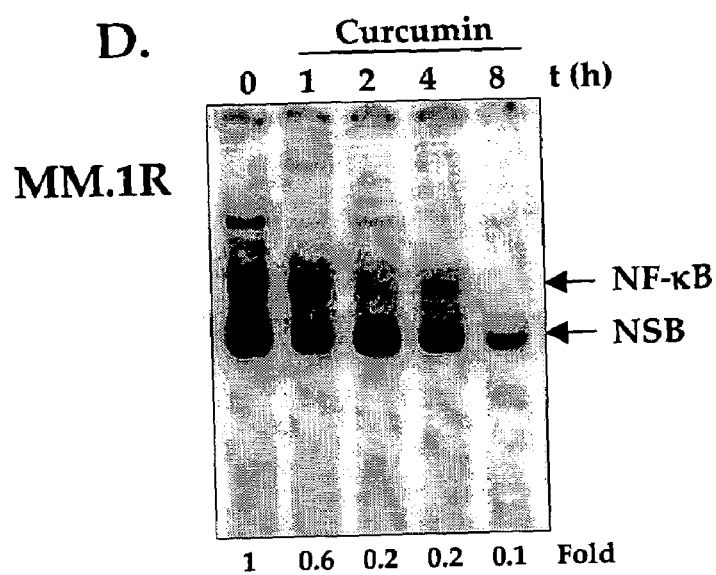
FIG. 1D: Effect of exposure duration on curcumin-induced NF-κB suppression in MM.1R cells. Cells were treated as described in FIG. 1B.

Curcumin has been shown to suppress NF-κB activation induced by various inflammatory stimuli and inhibit activation of IκB kinase activity needed for NF-κB activation. Curcumin also downregulates expression of various NF-κB-regulated genes including bcl-2, COX2, MMP-9, TNF, cyclin D1 and adhesion molecules. Moreover, curcumin has been reported to induce apoptosis in a wide variety of cells through sequential activation of caspase-8, BID cleavage, cytochrome C release, caspase-9, and caspase-3. Numerous studies in animals have demonstrated that curcumin has potent chemopreventive activity against a wide variety of different tumors (Rao et al., 1995; Kawamori et al., 1999), and administration of curcumin in humans even at 8 g per day has been shown to be safe in phase I clinical trials (Cheng et al., 1998).

Results presented herein indicate that NF-κB is constitutively active in all human multiple myeloma cell lines examined. Curcumin downregulated the nuclear pool, or active form of NF-κB and suppressed constitutive IκBα phosphorylation, IKK kinase activity, and expression of NF-κB-regulated gene products IκBα, Bcl-2, Bcl-$x_L$, cyclin D1, and interleukin-6. This led to suppression of proliferation, arrest of cells at the G1/S phase boundary of the cell cycle, and induction of apoptosis as indicated by the activation of caspase-7 and caspase-9 and PARP cleavage. Curcumin also induced chemosensitivity to vincristine.

All four multiple myeloma cell lines (U266, RPMI8226, MM.1 and MM.1R) used herein expressed constitutively active NF-κB. These results are in agreement with two recent reports that showed constitutive NF-κB in U266 and RPMI-8226 cells by electrophoretic mobility gel shift assay. MM.1 and MM.1R, a dexamethasone-resistant cell line, also express constitutive NF-κB. These results differ from those of Hideshima et al., who showed lack of constitutively active NF-κB in MM.1S cells which are same as MM.1 cells. Because constitutive activation of NF-κB leads to nuclear translocation of p65, the presence of nuclear p65 in all the cell lines examined by immunocytochemistry was confirmed. These results further indicate that multiple myeloma cells exhibit constitutively active IκB kinase which is the kinase required for NF-kB activation. This is the first report to show an elevated IκB kinase activity in multiple myeloma cells.

Suppression of constitutive NF-κB activation by curcumin in all four multiple myeloma cell lines examined herein is in agreement with previous reports that showed curcumin is a potent inhibitor of NF-κB activation. Curcumin inhibits NF-κB activation by blocking constitutively active IκB kinase present in multiple myeloma cells. Because curcumin inhibited IκB kinase activity both inside the cells and in vitro, it is suggested that curcumin may be a direct inhibitor of IκB kinase. Since recombinant IκB kinase enzyme was not employed, one can not completely rule out the possibility of indirect inhibition of IκB kinase by curcumin. In any case, curcumin appears to suppress IκB kinase activation which leads to inhibition of IκBα phosphorylation and thus abrogation of IκBα degradation. These results are in agreement with previous reports which showed inhibition of IκB kinase by curcumin in colon cancer cells and macrophages. A recent report showed that PS-1145, a rationally designed IκB kinase inhibitor, blocked TNF-induced NF-kB activation in MM.1 cells. The concentration of curcumin required to block IκB kinase activity in the cells was comparable to that reported for PS-1145.

Suppression of cell proliferation by curcumin in multiple myeloma cells is in agreement with previous reports that showed curcumin-induced suppression of NF-κB leads to inhibition of cellular proliferation of cutaneous T cell lymphoma and acute myelogenous leukemia. The results on the antiproliferative effects of curcumin are in agreement with those of Hideshima et al. who showed PS-1145, an IKK blocker, inhibits cell proliferation. These workers reported that 50 μM PS-1145 inhibits proliferation of multiple myeloma cell lines MM.1S, RPMI-8226 and U266 by less than 50%. In contrast, almost complete inhibition of proliferation of all these cell lines was found with as little as 10 μM curcumin.

Several potential mechanisms could explain why NF-κB downregulation by curcumin leads to suppression of proliferation of multiple myeloma cells. One of the potential mechanisms involves suppression of IL-6 production as shown herein. Numerous studies indicate that IL-6 is a potent growth factor for multiple myeloma cells. Whether IL-6 is a paracrine or an autocrine growth factor for multiple myeloma cells is highly controversial. In these studies it is unlikely, however, that curcumin suppressed the growth of multiple myeloma cells through suppression of IL-6 production because three out of the four cell lines examined produced no detectable IL-6. It is also unlikely that curcumin inhibits cell growth through downregulation of the constitutively active Stat3 signaling because proliferation of cells which do not express constitutively active Stat3 (e.g; RPMI 8226) are also inhibited by curcumin. In this study, curcumin downregulated bcl-2 and bcl-$x_L$ expression, the proteins that have been implicated in the cell survival of multiple myeloma cells. Thus it is possible that downregulation of bcl-2 and bcl-$x_L$ by curcumin could lead to suppression of multiple myeloma cell proliferation.

It was also found that multiple myeloma cells overexpress cyclin D1, another NF-κB-regulated gene, and that this expression is downregulated by curcumin. Overexpression of cyclin D1 has been noted in a wide variety of tumors, but its role in multiple myeloma cells has not been reported. Given that cyclin D1 is needed for cells to advance from the G1 to S phase of the cell cycle, induction of G1/S arrest and thus suppression of multiple myeloma cell proliferation by curcumin may very well resulted from downregulation of cyclin D1.

Suppression of NF-κB by curcumin also led to apoptosis of multiple myeloma cells as indicated by activation of caspases and cleavage of PARP. These results are in agreement with reports indicating that NF-κB mediates antiapoptotic effects. Downregulation of NF-κB also sensitized multiple myeloma cells to vincristine. Even the MM.1R cells, which have been shown to be resistant to dexamethasone, were sensitive to curcumin.

Multiple myeloma is an incurable aggressive B cell malignancy, and more than 90% of multiple myeloma patients become chemoresistant. Several agents have been tested in the search for more effective treatment of multiple myeloma. These include PS341, a proteosome inhibitor, and thalidomide, an inhibitor of TNF production. Nonspecific drug-toxicity is one of the major problems in drug development. However, numerous studies have shown that curcumin is pharmacologically safe. It was recently demonstrated in phase 1 clinical trials that humans can tolerate up to 8 grams of curcumin per day when taken orally (Cheng et al., 1998). Furthermore, curcumin has been shown to downregulate the expression of ICAM-1, VCAM-1 and ELAM-1, all NF-κB-regulated gene products that have been implicated in activation of stromal cells by multiple myeloma cells. TNF, another cytokine known to play a pathological role in multiple myeloma, has also been shown to be downregulated by curcumin. The results presented herein clearly demonstrate that curcumin can suppress NF-κB, IKK, bcl-2, bcl-$x_L$, cyclin D1 and cell proliferation in multiple myeloma cells. These results provide enough rationale for considering curcumin worthy of clinical trial in patients with multiple myeloma.

As used herein, "multiple myeloma cells" refer to multiple myeloma cell lines or CD138$^+$ plasma cells isolated from multiple myeloma patients.

In the present invention, there are provided methods of inhibiting proliferation of multiple myeloma cells, inducing apoptosis in multiple myeloma cells and increasing the cytotoxic effects of chemotherapeutic agent against multiple myeloma cells by treatment with curcumin. In general, the chemotherapeutic agent can be vincristine, BCNU, melphalan, cyclophosphamide, Adriamycin, prednisone or dexamethasone.

The present invention is also directed to methods of treating multiple myeloma in an individual and increasing the cytotoxic effects of chemotherapeutic agent against multiple myeloma cells in an individual by treatment with curcumin. In general, the chemotherapeutic agents are those listed above.

It is specifically contemplated that methods of the present invention utilize pharmaceutical compositions comprising curcumin, e.g. a pharmaceutical composition comprising curcumin and a pharmaceutically acceptable carrier that is well known and routinely used in the art. In view of the published clinical trials (Cheng et al., 1998) and other studies involving the use of curcumin, a person having ordinary skill in this art would readily be able to determine, without undue experimentation, the appropriate dosages and routes of administration of curcumin in the methods of the present invention. When used in vivo for therapy, curcumin is administered to the patient or an animal in therapeutically effective amounts, i.e., amounts that inhibit proliferation of multiple myeloma cells, induce apoptosis in multiple myeloma cells or increase cytotoxic effects of chemotherapeutic agent against multiple myeloma cells, e.g., administered in a dose of from about 0.01 mg/kg of the individual's body weight to about 500 mg/kg of the individual's body weight.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cells and Reagent

Human multiple myeloma cell lines U266, RPMI 8226, and MM.1 were obtained from the American Type Culture Collection (Rockville, Md.). Cell lines U266 (ATCC#TIB-196) and RPMI 8226 (ATCC#CCL-155) are plasmacytomas of B cell origin. U266 is known to produce monoclonal antibodies and IL-6. RPMI 8226 produces only immunoglobulin light chains and there is no evidence for heavy chain or IL-6 production. Doxorubicin (Dox-6)- and melphalan (LR-5)-resistant clones of RPMI 8226 were provided by Dr. Willium Dalton (H. Lee Moffitt Cancer Center and Research Institute, Tampa, Fla.)

The MM.1 (also called MM.1S) cell line, which is established from the peripheral blood cells of a patient with IgA myeloma, secretes lambda light chain, is negative for the presence of EBV genome, and expresses leukocyte antigen DR, PCA-1, T9 and T10 antigens. MM.1R is a dexamethasone-resistant variant of MM.1 cells. These two cell lines was provided by Dr. Steve T. Rosen of Northwestern University Medical School (Chicago, Ill.).

Rabbit polyclonal antibodies to IkBa, p50, p65, cyclin D1, Bcl-2, Bcl-$x_L$, and PARP and STAT3 were purchased from Santa Cruz Biotechnology (Santa Cruz, Calif.). Antibodies against cleaved-PARP, phospho-IkBa, procaspase-7, procaspase-9 and the polynucleotide kinase kit were purchased from New England Biolabs, Inc. (Beverly, Mass.). Anti-IKKa and anti-IKKb antibody were kindly provided by Imgenex (San Diego, Calif.). Goat anti-rabbit-HRP conjugate was purchased from Bio-Rad Laboratories (Hercules, Calif.), goat anti-mouse-HRP was purchased from Transduction Laboratories (Lexington, Ky.) and goat anti-rabbit-Alexa 594 was purchased from Molecular Probes (Eugene, Oreg.). Anti-CD138 microbeads and PE-conjugated anti-CD138 were purchased from Miltenyi Biotech (Auburn, Calif.)

Cell-permeable NEMO (NF-κB essential modifier; also called IKKγ)-binding domain peptide (NBD), NH$_2$-DR-QIKIWFQNRRMKWKKTALDWSWLQTE-CONH$_2$, (SEQ ID NO. 2) and control peptide NEMO-C, NH$_2$-DRQIKIWFQNRRMKWKK-CONH$_2$ (SEQ ID NO. 3) were obtained from Imgenex (San Diego, Calif.).

Curcumin was purchased from LKT Laboratories, Inc. (St. Paul, Minn.) and was prepared as a 20 mM solution in dimethyl sulfoxide and then further diluted in cell culture medium. Vincristine, Hoechst 33342 and MTT were purchased from Sigma-Aldrich Chemicals (St. Louis, Mo.). RPMI-1640, fetal bovine serum (FBS), 0.4% trypan blue vital stain and 100× antibiotic-antimycotic mixture were obtained from Life Technologies Inc. (Grand Island, N.Y.). Protein A/G-Sepharose beads were obtained from Pierce (Rockford, Ill.). g-P$^{32}$-ATP was from ICN Pharmaceuticals (Costa Mesa, Calif.). Human IL-6 kit was purchased from BioSource International (Camarillo, Calif.). Ultrafree 4 centrifugal filters were purchased from Millipore Corporation (Bedford, Mass.).

All the human multiple myeloma cell lines were cultured in RPMI 1640 medium containing 1× antibiotic-antimycotic. U266, MM.1, and MM.1R were cultured in 10% FBS, whereas cell line RPMI 8226 was grown in 20% FBS. Occasionally, cells were examined by Hoechst staining and by custom PCR for mycoplasma contamination.

EXAMPLE 2

Preparation of Nuclear Extracts for NF-κB

Nuclear extracts were prepared according to Bharti et al. (2003). Briefly, 2×10$^6$ cells were washed with cold PBS and suspended in 0.4 ml of hypotonic lysis buffer containing protease inhibitors for 30 min. The cells were then lysed with 12.5 μl of 10% Nonidet P-40. The homogenate was centrifuged, and supernatant containing the cytoplasmic extracts was stored frozen at −80° C. The nuclear pellet was resuspended in 25-μl ice-cold nuclear extraction buffer. After 30 min of intermittent mixing, the extract was centrifuged, and supernatants containing nuclear extracts were collected. Protein content was measured by the Bradford method. If the supernatants were not used immediately, they were stored at −80° C.

EXAMPLE 3

Electrophoretic Mobility Shift Assay for NF-κB

NF-kB activation was analyzed by electrophoretic mobility gel shift assay (EMSA) as described previously (Chaturvedi et al., 1994). In brief, 8-μg nuclear extracts prepared from curcumin-treated or untreated cells were incubated with $^{32}$P end-labeled double-stranded 45-mer of NF-kB oligonucleotide from human immunodeficiency virus-1 long terminal repeat (5'-TTGTTACAA GGGACTTTCCGCT GGGGACTTTCCAG GGAG-GCGTGG-3', SEQ ID NO. 4) for 15 min at 37° C., and the DNA-protein complex was resolved in a 6.6% native polyacrylamide gel. Radioactive bands from the dried gels were visualized and quantitated by PhosphorImager (Molecular Dynamics, Sunnyvale, Calif.) using ImageQuant software.

EXAMPLE 4

Immunocytochemistry for NF-κB P65 and STAT3

Untreated or treated multiple myeloma cells were plated on a poly-L-lysine-coated glass slide by centrifugation using a Cytospin 4 (Thermoshendon, Pittsburg, Pa.), air-dried for 1 h at room temperature, and fixed with cold acetone. After a brief washing in PBS, slides were blocked with 5% normal goat serum for 1 h and then incubated either with rabbit polyclonal anti-human NF-κB p65 antibody (SC-109; dilution, 1:100) or with anti-human STAT3 antibody (SC-482; dilution, 1:100). After overnight incubation, the slides were washed and then incubated with goat anti-rabbit IgG-Alexa 594 (A-11037; dilution, 1:100) for 1 h and counter-stained for nuclei with Hoechst (50 ng/ml) for 5 min. Stained slides were mounted with mounting medium (Sigma Colo.) and analyzed under an epifluorescence microscope (Labophot-2, Nikon, Tokyo, Japan). Pictures were captured using Photometrics Coolsnap CF color camera (Nikon, Lewisville, Tex.) and MetaMorph version 4.6.5 software (Universal Imaging Corp., Downingtown Pa.). Cells with nuclear staining of NF-κB p65 or STAT3 were counted separately. One hundred cells were counted for each specimen, and the sample was graded on the basis of a 4-point scale: −, no nuclear positive cells (0%); +, low number of nuclear positive cells (<10%); ++, moderate number of nuclear positive cells (10–50%); +++, high number of nuclear positive cells (>50%).

EXAMPLE 5

Western Blot

Thirty to fifty micrograms of cytoplasmic protein extracts prepared as described (Chaturvedi et al., 2000) were resolved on 10% SDS-PAGE gel. After electrophoresis, the proteins were electrotransferred to a nitrocellulose membrane, blocked with 5% nonfat milk, and probed with antibodies against either IkBa, phospho-IkBa, Bcl-2, Bcl-$x_L$, or cyclin D1 (1:3000) for 1 h. Thereafter, the blot was washed, exposed to HRP-conjugated secondary antibodies for 1 h, and finally detected by chemiluminescence (ECL, Amersham Pharmacia Biotech., Arlington Heights, Ill.).

For detection of cleavage products of PARP, whole cell extracts were prepared by lysing curcumin-treated cells in lysis buffer (20 mM Tris, pH 7.4, 250 mM NaCl, 2 mM EDTA, pH 8.0, 0.1% Triton-X100, 0.01 mg/ml aprotinin, 0.005 mg/ml leupeptin, 0.4 mM PMSF, and 4 mM NaVO$_4$). Lysates were then spun at 14000 rpm for 10 min to remove insoluble material, resolved on 7.5% gel and probed with PARP antibodies. PARP was cleaved from the 116-kDa intact protein into 85-kDa and 40-kDa peptide products. To detect cleavage products of procaspase 7 and procaspase 9, whole cell extracts were resolved on 10% gel and probed with appropriate antibodies.

EXAMPLE 6

IkB Kinase Assay

The IkB kinase assay was performed with a modified method as described earlier (Manna et al., 2000). Briefly, 200 μg cytoplasmic extracts were immunoprecipitated with 1 μg of anti-IKKa and IKKb antibodies each, and the immune complexes so formed were precipitated with 0.01 ml of protein A/G-Sepharose beads for 2 hour. The beads were washed first with lysis buffer and then with kinase assay buffer (50 mM HEPES pH 7.4, 20 mM MgCl$_2$, and 2 mM DTT). The immune complex was then assayed for kinase activity using kinase assay buffer containing 20 mCi [g-P$^{32}$]ATP, 10 μM unlabeled ATP, and 2 μg/sample glutathione S-transferase-IkBa (1–54). After incubation at 30° C. for 30 min, the reaction was stopped by boiling the solution in 6×SDS sample buffer. Then the reaction mixture was resolved on 12% SDS-PAGE. Radioactive bands of the dried gel were visualized and quantitated by PhosphorImager.

To determine the total amount of IKK complex in each sample, 60 mg of cytoplasmic protein was resolved on a 7.5% acrylamide gel and then electrotransferred to a nitrocellulose membrane. The membrane was blocked with 5% nonfat milk protein for 1 h and then incubated with either anti-IKKα or anti-IKKβ antibodies for 1 h. The membrane was then washed and treated with HRP-conjugated secondary anti-mouse IgG antibody and finally detected by chemiluminescence (Amersham Pharmacia Biotech, Arlington Heights, Ill.).

EXAMPLE 7

Proliferation Assay

The antiproliferative effects of curcumin against different multiple myeloma cell lines were determined by the MTT dye uptake method as described earlier (Manna et al., 1998). Briefly, cells (5000/well) were incubated in triplicate in a 96-well plate in the presence or absence of indicated test samples in a final volume of 0.1 ml for 24 h at 37° C. Thereafter, 0.025 ml of MTT solution (5 mg/ml in PBS) was added to each well. After a 2 h incubation at 37° C., 0.1 ml of extraction buffer (20% SDS, 50% dimethylformamide) was added. Incubation was continued for overnight at 37° C., and then the OD at 590 nm was measured using a 96-well multiscanner autoreader (Dynatech MR 5000), with extraction buffer as blank. Percent cell viability=(OD of the experiment samples/OD of the control)×100.

The antiproliferative effects of curcumin were also monitored by the thymidine incorporation method. Five thousand cells in 100 ml medium were cultured in triplicate in 96-well plates in the presence or absence of curcumin for 24 h. Six hours before the completion of experiment, the cells were pulsed with 0.5 mCi $^3$H-thymidine, and the uptake of $^3$H-thymidine was monitored using a Matrix-9600 b-counter (Packard Instruments, Downers Grove, Ill.).

EXAMPLE 8

Flow Cytometric Analysis

To determine the effect of curcumin on cell cycle, multiple myeloma cells were treated for different times, washed, and fixed with 70% ethanol. After incubation for overnight at –20° C., cells were washed with PBS prior to staining with propidium iodide (PI), and then suspended in staining buffer (PI, 10 mg/ml; Tween-20, 0.5%; RNase, 0.1% in PBS). The cells were analyzed using a FACS Vantage flow cytometer that uses CellQuest acquisition and analysis programs (Becton Dickinson, San Jose, Calif.).

EXAMPLE 9

Determination of IL-6 Protein

Supernatants were collected from untreated or curcumin-treated multiple myeloma cell cultures and concentrated approximately 20-fold using Ultrafree 4 centrifugal filters with Biomax-10K NMWL Membrane (Millipore). One hundred microliter aliquots were removed, and IL-6 contents were determined by an ELISA kit (Biosource International).

EXAMPLE 10

Curcumin Suppresses Constitutive NF-κB Expressed by Multiple Myeloma Cells

The NF-kB status in four different multiple myeloma cell lines was first investigated by electrophoretic mobility gel shift assay (EMSA). The results shown in FIG. 1 indicate that all four cell lines expressed constitutively active NF-κB, resolved as an upper and a lower bands. The effect of curcumin on constitutively active NF-κB was then investigated by examining the dose of curcumin required for complete suppression of NF-κB. U266 cells were treated with different concentrations of curcumin for 4 h and then examined for NF-κB by EMSA. Densitometric analysis of the retarded radiolabeled probe showed a decrease in NF-κB DNA binding activity. These results showed that 50 μM curcumin was sufficient to fully suppress constitutive NF-κB activation in U266 cells (FIG. 1A).

Figure 1E:
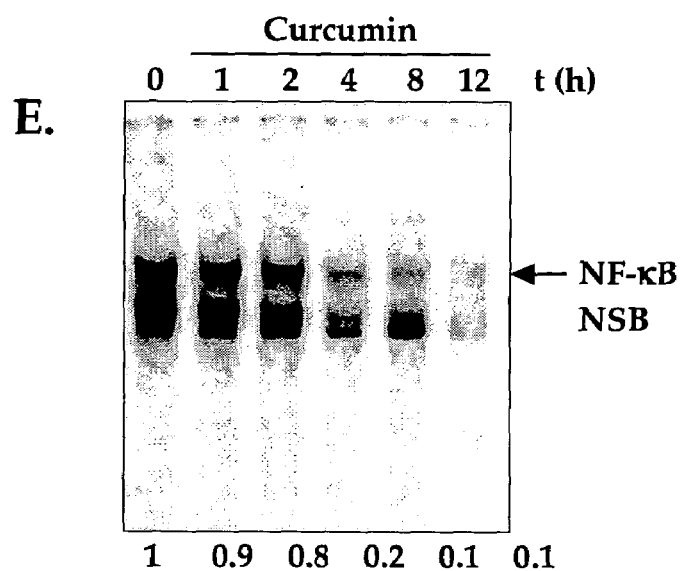
FIG. 1E: Effect of exposure duration on curcumin-induced NF-κB suppression in RPMI 8226. Cells were treated as described in FIG. 1B.
Figure 1F:
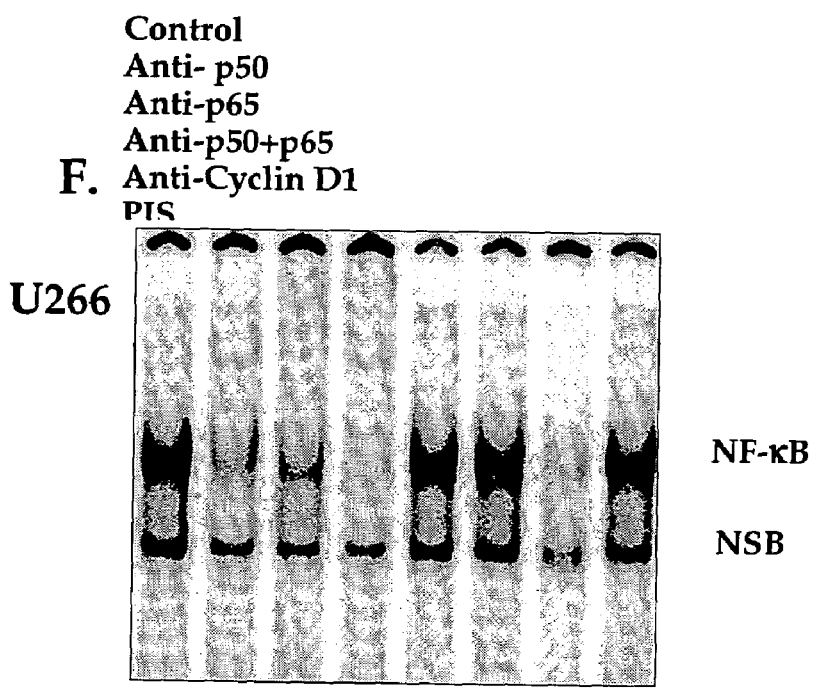
FIG. 1F: The binding of NF-κB to DNA is specific and consists of p50 and p65 subunits. Nuclear extracts were prepared from U266 cells ($2\times10^6$/ml), incubated for 30 min with different antibodies or unlabeled NF-κB oligonucleotide probe, and then assayed for NF-κB by EMSA.

The minimum duration of exposure to curcumin required for suppression of NF-kB was then examined. Multiple myeloma cells were incubated with 50 μM curcumin for different times, then nuclear extracts were prepared and examined for NF-κB by EMSA. The results showed that curcumin downregulated constitutive NF-κB in all four cell lines but with different kinetics. Complete downregulation of NF-κB occurred at 4 h in U266 (FIG. 1B), MM.1 (FIG. 1C) and MM.1R (FIG. 1D) cells, whereas it took 8 h to downregulate NF-kB in RPMI8226 cells (FIG. 1E). Curcumin downregulated only the upper band and not lower band of NF-κB in most cases. In the case of RPMI 8226 cells, both bands were downregulated.

Since NF-kB is a family of proteins, and various combinations of Rel/NF-kB protein can constitute an active NF-kB heterodimer that binds to a specific DNA sequence. To show that the retarded band visualized by EMSA in multiple myeloma cells was indeed NF-kB, nuclear extracts from the multiple myeloma cells were incubated with antibody to either the p50 (NF-kB1) or the p65 (RelA) subunit of NF-kB. Both shifted the band to a higher molecular mass (FIG. 1F), thus suggesting that the major NF-kB band in the multiple myeloma cells consisted of p50 and p65 subunits. A nonspecific minor band which was not supershifted by the antibody was observed in some multiple myeloma cell lines. Neither preimmune serum nor the irrelevant antibody such as anti-cyclin D1 had any effect. Excess unlabeled NF-kB (100-fold), but not the mutated oligonucleotides, caused complete disappearance of the band.

Figure 2:
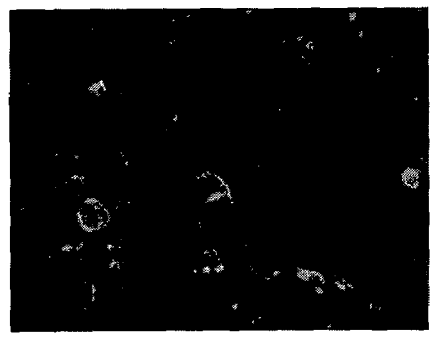
FIG. 2 shows that curcumin induces redistribution of p65. U266 and RPMI 8226 cells were incubated alone or with curcumin (50 μM) for 4 hours and then analyzed for the distribution of p65 by immunocytochemistry. Red stain indicates the localization of p65 and blue stain (Hoechst) indicates nucleus (magnification 200×).
Figure 2:
Figure 2:
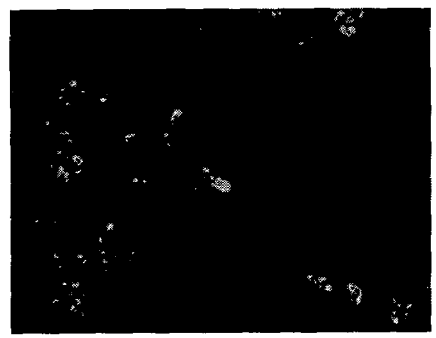
Figure 2:
Figure 2:
Figure 2:
Figure 2:
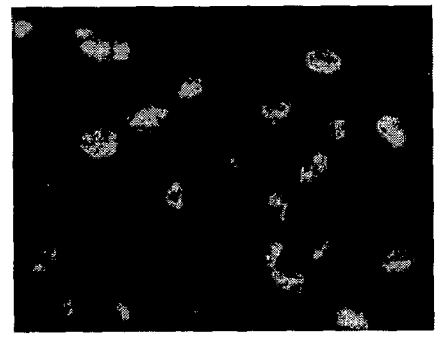
Figure 2:
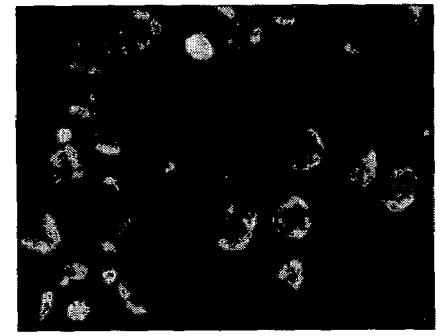

When NF-κB is activated, the p65 subunit of the NF-κB containing transactivation domain is translocated to the nucleus. In the inactive state, the p65 subunit of NF-kB is retained in the cytoplasm. Immunocytochemistry was then used to confirm that curcumin suppresses nuclear retention of p65. Curcumin-treated and untreated cells were cytospun on a glass slide, immunostained with anti-p65 antibody, and then visualized by the Alexa-594 conjugated second antibody as described above. The results in FIG. 2 clearly demonstrate that curcumin prevented the translocation of the p65 subunit of NF-κB to the nucleus in all four multiple myeloma cell lines. These cytological findings were consistent with the NF-κB inhibition observed by EMSA.

EXAMPLE 11

Curcumin Inhibits IκBα Phosphorylation and IκB Kinase Activity

Figure 3A:
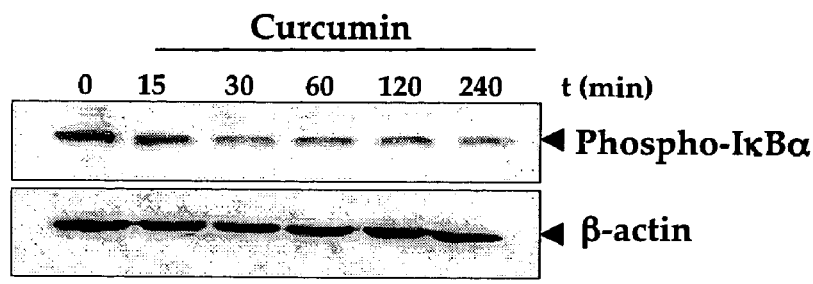
FIG. 3A: Level of phosphorylated IκBα determined by Western blotting.

The degradation of IκBα and subsequent release of NF-κB (p65:p50) requires prior phosphorylation at ser 32 and ser 36 residues. Therefore, in order to investigate whether the inhibitory effect of curcumin is mediated through alteration of IκBα phosphorylation, U266 cells were treated with curcumin and their protein extracts were checked for phospho-IκBα expression. Results in FIG. 3A show that untreated U266 cells constitutively expressed ser 32-phosphorylated IκBα. Upon curcumin treatment, the phosphorylated IκBα content decreased rapidly.

Figure 3B:
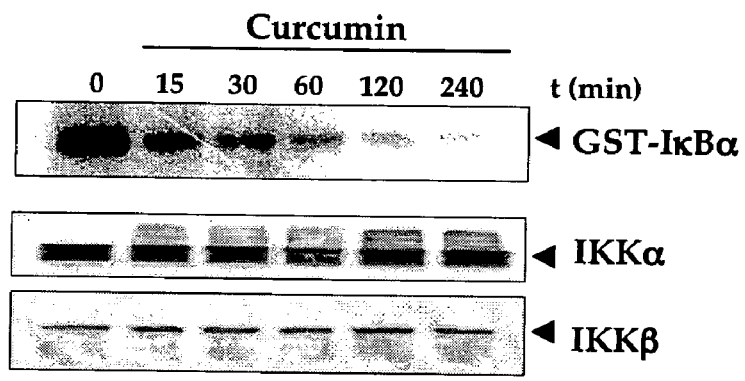
FIG. 3B: Immunoprecipitated IκB kinase and kinase assay of IκB kinase activity (upper panel) or Western blotting for the analysis of total IKKα and IKKβ proteins in cytoplasmic extracts (lower panel).

Phosphorylation of IkBa is mediated through IκB kinase. In vitro kinase assay using immunoprecipitated IκB kinase from untreated U266 cells and GST-IκBα as substrate showed constitutive IκB kinase activity, whereas under similar conditions IκB kinase immunoprecipitated from curcumin-treated cells showed a decreased in kinase activity that corresponded to the duration of curcumin treatment (FIG. 3B; upper panel). However, immunoblotting analysis of cell extracts from untreated and curcumin-treated cells showed no significant change in the protein levels of IκB kinase subunits IKKα and IKKβ (FIG. 3B; middle and lower panel).

Figure 3C:
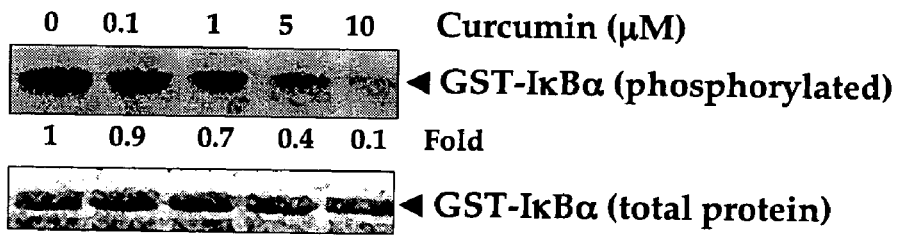
FIG. 3C: IκB kinase was immunoprecipitated and kinase assay was performed in the absence or presence of the indicated concentrations of curcumin (upper panel). Lower panel indicates the amount of GST-IκBα protein stained with Coomassie Blue in each well in the same dried gel.

IκB kinase has been shown to be regulated by several upstream kinases. To determine if curcumin acted as a direct inhibitor of IκB kinase activity, IκB kinase was immunoprecipitated from untreated U266 cells and then treated with different concentrations of curcumin for 30 min. After the treatment, the samples were examined for IκB kinase activity using GST-IκBα as a substrate. Results in FIG. 3C (upper panel) showed that curcumin inhibited IκB kinase activity directly in a dose-dependent manner. These results suggest that curcumin is a direct inhibitor of IκB kinase. Since purified IκB kinase was not used the possibility that curcumin suppressed an upstream kinase required for IκB kinase activation can not be completely ruled out.

EXAMPLE 12

Curcumin Downregulates the Expression of NF-κB-Regulated Gene Products

Because IκBα, Bcl-2, Bcl-$x_L$, and cyclin D1 have all been shown to be regulated by NF-κB, the effect of curcumin on the expression of these gene products was examined by immunoblotting. As depicted in FIG. 4, all four gene products were expressed in U266 cells. Treating cells with curcumin downregulated the pools of IκBα (FIG. 4A), Bcl-2 (FIG. 4B), Bcl-$x_L$ (FIG. 4C) and cyclinD1 (FIG. 4E) proteins in a time-dependent manner, although the kinetics of suppression were different. Cyclin D1 showed the most abrupt and complete depletion within 4 hours of curcumin treatment. Bcl-2 also showed a complete decline but it achieved the lowest level by 8 hours. On the other hand IκBα and Bcl-xL showed only a partial decline.

Figure 4A:
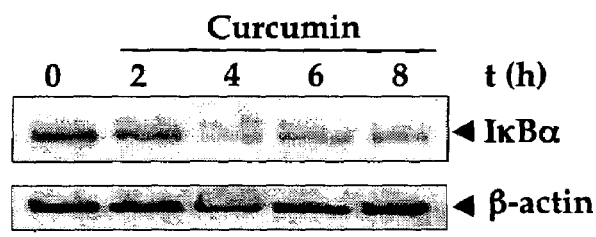
FIG. 4 shows the effect of curcumin on NF-κB regulated gene products. Two million U266 cells were treated with curcumin (50 μM) for the indicated times, and cytoplasmic extracts were prepared. Sixty micrograms of cytoplasmic extracts were resolved on 10% SDS-PAGE gel, electrotransferred on a nitrocellulose membrane, and probed for the following: IκBα (FIG. 4A); Bcl-2 (FIG. 4B); Bcl-$x_L$ (FIG. 4C) and cyclin D1 (FIG. 4D). The same blots were stripped and reprobed with anti-β-actin antibody to show equal protein loading (lower panel in each figure).
FIG. 4E: Curcumin downregulates IL-6 production. U266, MM.1 or RPMI 8226 cells ($1\times10^7$) were treated with curcumin (10 mM) in 5 ml of medium for the indicated times. Supernatants were harvested and concentrated approximately 20×, and IL-6 was quantitated by an IL-6 ELISA kit. Values shown were normalized to 1 ml of un-concentrated supernatants.
Figure 4B:
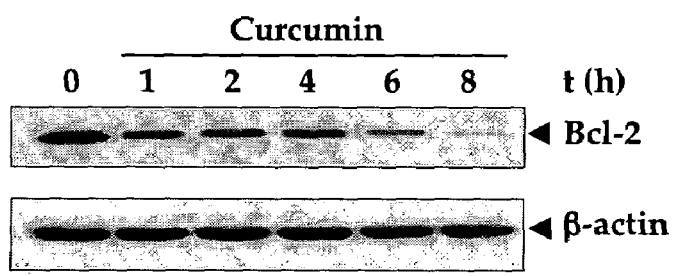
Figure 4C:
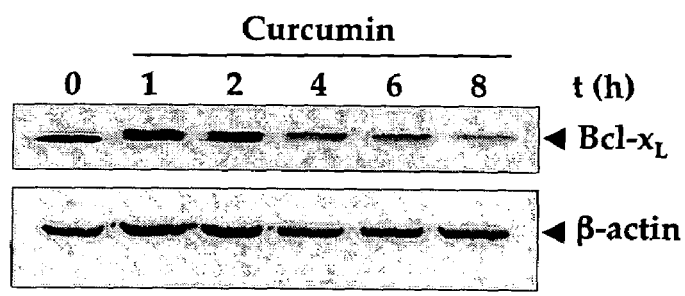
Figure 4D:
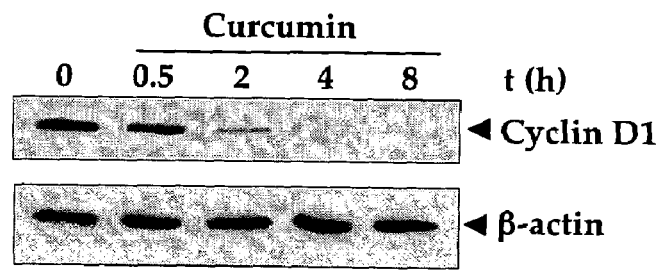
Figure 4E:
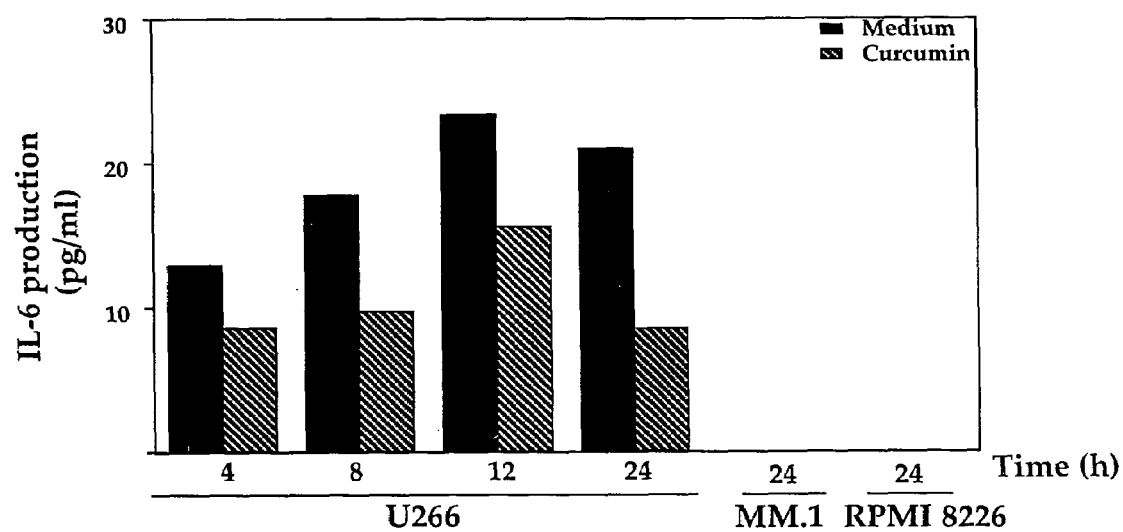
Figure 5A:
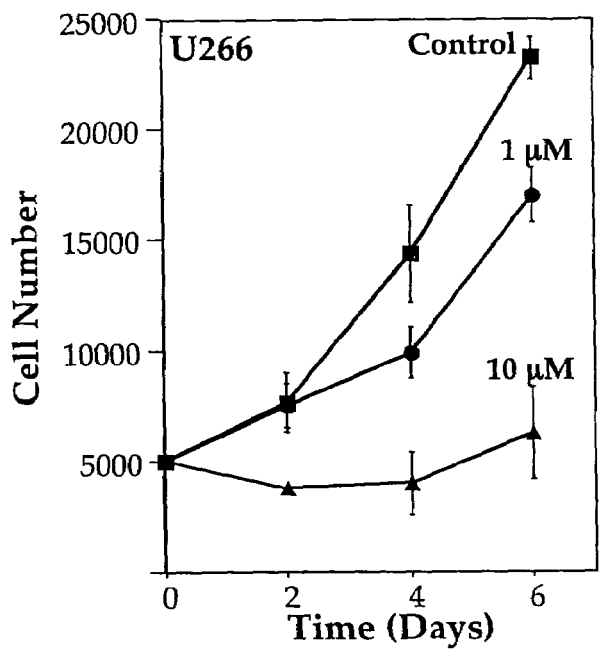
FIG. 5 shows the curcumin inhibits the growth of human multiple myeloma cells. U266 (FIG. 5A); RPMI 8226 (FIG. 5B); MM.1 (FIG. 5C) or MM.1R cells (FIG. 4D) (5000 cells/0.1 ml) were incubated at 37° C. with curcumin (1 mM or 10 mM) for the indicated times and viable cells were counted using standard trypan blue dye exclusion test. The results are shown as the mean (±s. d.) cell count from triplicate cultures.
Figure 5B:
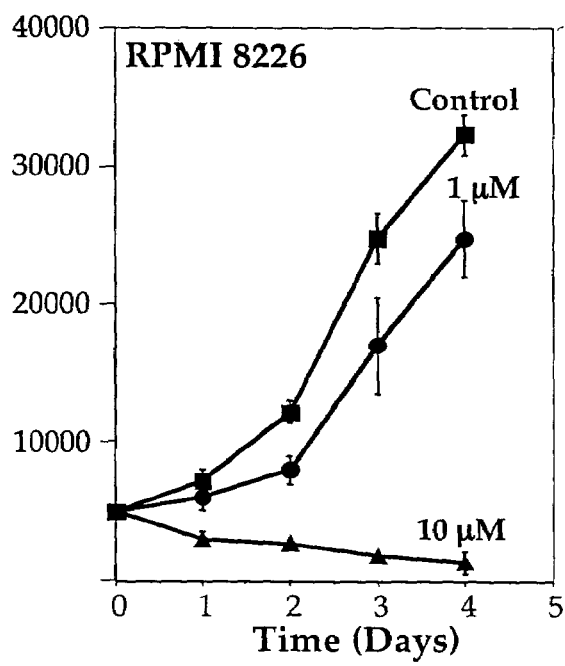
Figure 5C:
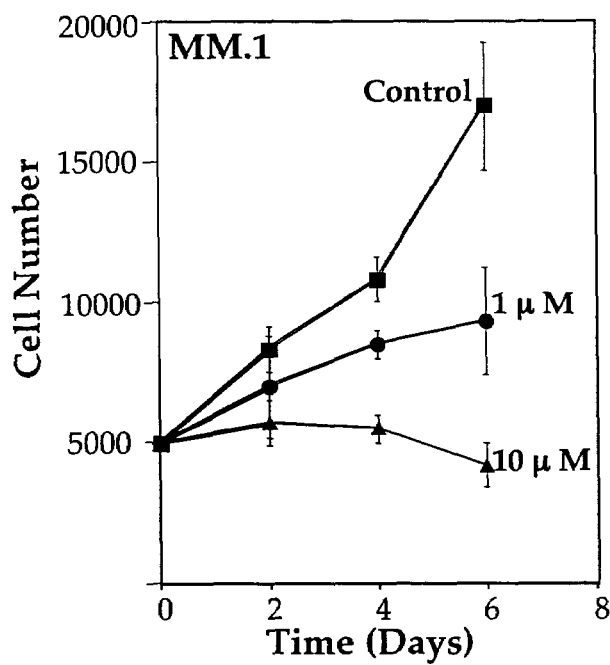
Figure 5D:
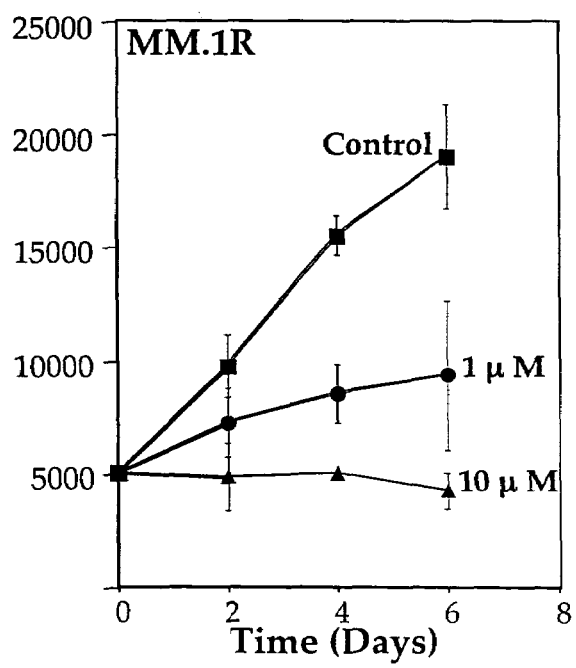

Interleukin-6 is another NF-kB-regulated gene and has been shown to serve as a growth factor for multiple myeloma cells. U-266 cells produced a significant amount of IL-6 protein in a time-dependent manner whereas neither MM.1 nor RPMI 8226 produced any detectable amount of IL-6 as measured by ELISA (FIG. 4E). As shown in FIG. 4E, curcumin treatment inhibited the production of IL-6 by U266 cells.

EXAMPLE 13

Curcumin Suppresses Proliferation of Multiple Myeloma Cells

Because NF-κB has been implicated in cell survival and proliferation, the effect of curcumin on the proliferation of multiple myeloma cell lines was examined. U266, RPMI 8226, MM.1, and MM.1R cells were cultured in the presence of different concentrations of curcumin, and the number of viable cells was examined by trypan blue dye-exclusion method.

Results in FIG. 5 show that curcumin at a concentration as low as 1 μM inhibited the growth of U266 (panel A), RPMI 8226 (panel B), MM.1 (panel C) and MM.1R (panel D) by 27%, 23%, 45% and 51% respectively. At 10 μM curcumin completely suppressed the growth in all cell lines. These results indicate that curcumin suppresses the proliferation of all multiple myeloma cell lines tested, including MM.1R that is resistant to dexamethasone-induced apoptosis.

Figure 6A:
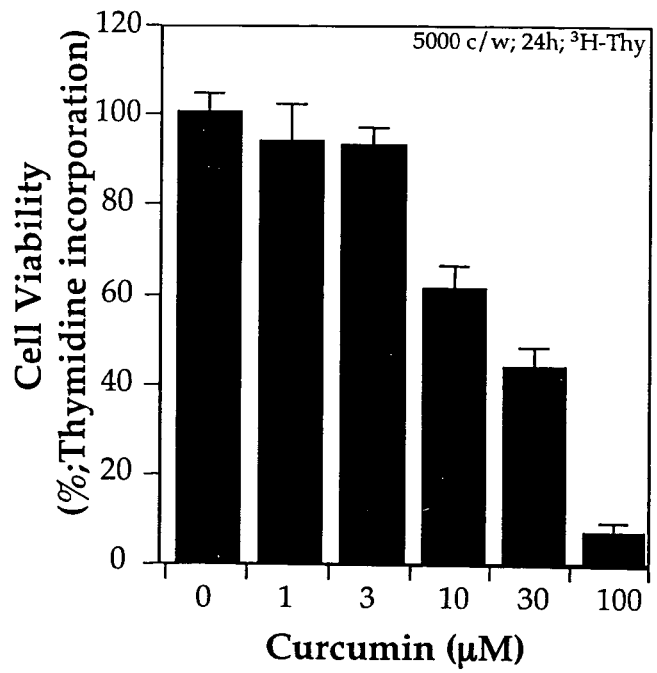
FIG. 6A: U266 cells (5000 cells/0.1 ml) were incubated with different concentrations of curcumin for 24 hours, and cell proliferation assay was performed as described. Results are shown as mean (±s.d.) of percent [$^3$H]-thymidine incorporation of triplicate cultures compared to untreated control.
Figure 6B:
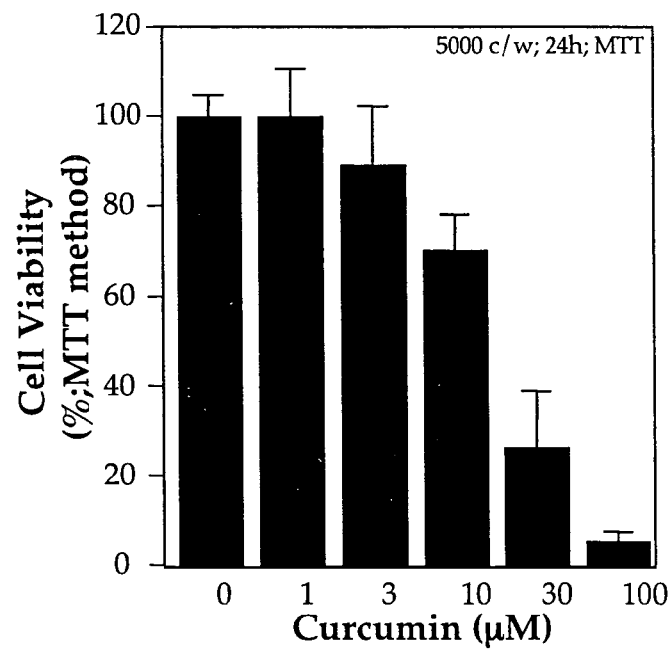
FIG. 6B: U266 cells (5000 cells/0.1 ml) were incubated with different concentrations of curcumin for 24 hours, and cell viability was determined by MTT method. The results are shown as the mean (±s.d.) percent viability from triplicate cultures.

The antiproliferative effects of curcumin was also examined by thymidine incorporation in U266 cells. Curcumin suppressed thymidine incorporation within 24 h in a dose-dependent manner (FIG. 6A). Results in MTT assays, which indicates mitochondrial activity of the cells, showed that curcumin suppressed mitochondrial activity of U266 cells within 24 h and the suppression occurred in a dose-dependent manner (FIG. 6B).

EXAMPLE 14

Curcumin Induces Apoptosis in Multiple Myeloma Cells

Whether suppression of NF-κB in multiple myeloma cells also leads to apoptosis was investigated. One of the hallmarks of apoptosis is activation of caspases. U266 cells were treated with curcumin for different times, and whole cell extracts were prepared and analyzed for activation of caspase-9 (an upstream caspase), caspase-7 (a downstream caspase) and cleavage of PARP, a well-known substrate for caspase-3, -6 and -7.

Figure 6C:
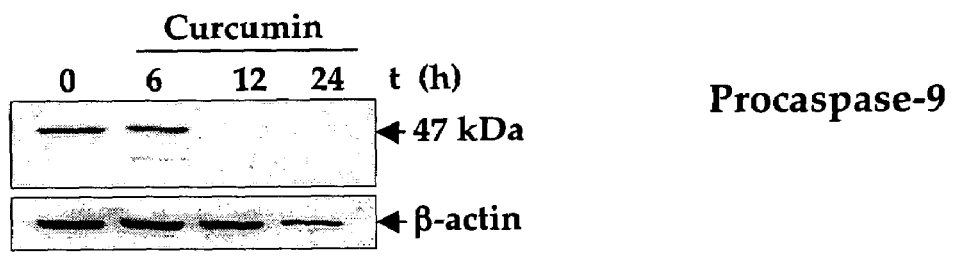
FIG. 6C-E shows that U266 cells ($2\times10^6$ cells/ml) were incubated in the absence or presence of curcumin (50 μM) for indicated times. The cells were washed and total proteins were extracted by lysing the cells. Sixty microgram of extracts were resolved on 10% SDS-PAGE gel, electrotransferred to a nitrocellulose membrane, and probed with anti-procaspase-9 (FIG. 6C), anti-procaspase-7 (FIG. 6D), anti-PARP (FIG. 6E, upper panel) and anti-cleaved PARP (FIG. 6E, lower penal).
Figure 6D:
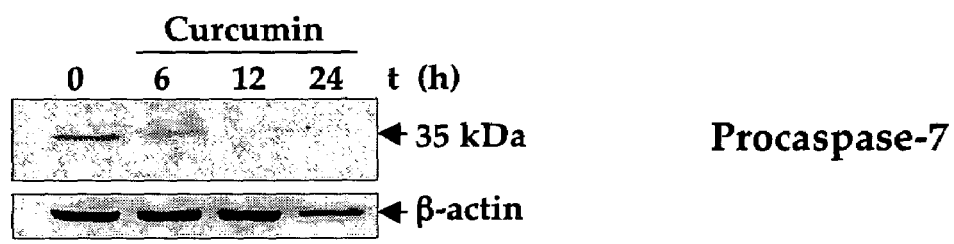
Figure 6E:
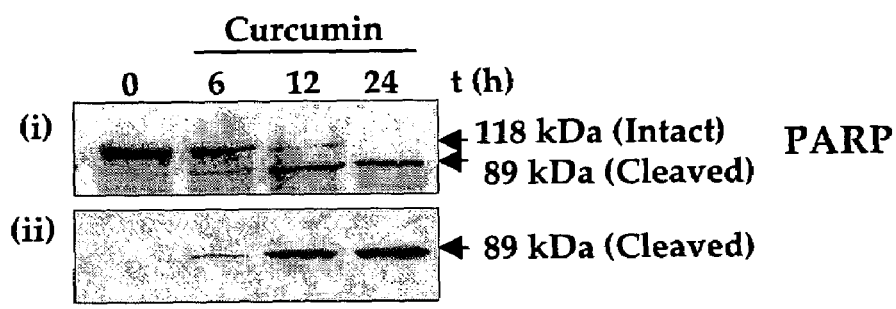

Immunoblot analysis of extracts from cells treated with curcumin clearly showed a time-dependent activation of caspase-9 (FIG. 6C) and caspase-7 (FIG. 6D) as indicated by the disappearance of the 47-kDa and 35-kDa bands, respectively. Activation of downstream caspases lead to the cleavage of a 118-kDa PARP protein into an 89-kDa fragment, another hallmark of cells undergoing apoptosis (FIG. 6E), whereas untreated cells did not show any PARP cleavage. Increasing amount of the 89-kDa fragment was also detected by antibodies that recognize only the cleaved 89-kDa PARP species (FIG. 6E, lower panel). Taken together, these results clearly demonstrate that curcumin induces apoptosis in multiple myeloma cells.

EXAMPLE 15

Curcumin Arrests Cells at the G1/S Phase of the Cell Cycle

D-type cyclins are required for the progression of cells from the G1 phase of the cell cycle to S phase (DNA synthesis). Since a rapid decline of cyclin D1 was observed in curcumin-treated multiple myeloma cells, the effect of curcumin on U266 cell cycle was determined next.

Figure 7:
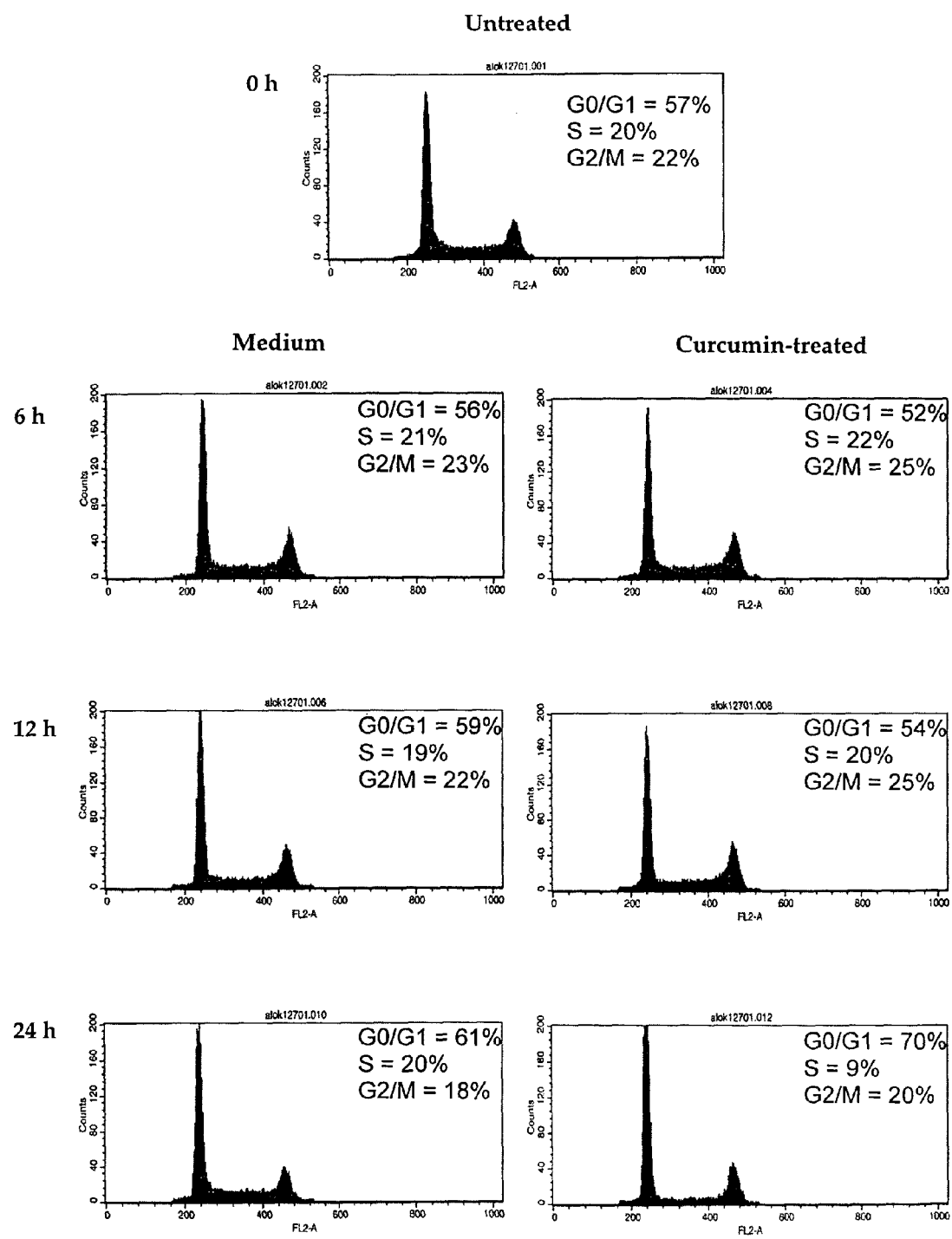
FIG. 7 shows that curcumin arrests cells at the G1/S phase of the cell cycle. U266 cells ($2\times10^6$ cells/ml) were incubated in the absence or presence of curcumin (10 μM) for the indicated times. The cells were then washed, fixed, stained with propidium iodide, and analyzed for DNA content by flow cytometry.

Flow cytometric analysis of DNA from curcumin-treated cells showed a significant increase in the percentage of cells in the G1 phase (from 52% to 70%) and a decrease in the percentage of cells in the S phase (from 22% to 9%) within 24 h of treatment with 10 μM curcumin (FIG. 7). These results clearly show that curcumin induces G1/S arrest of the cells.

EXAMPLE 16

NEMO-Binding Domain (NBD) Peptide Suppresses Constitutive NF-κB and Proliferation of Multiple Myeloma Cells IKK is composed of IKKα, IKKβ and IKKγ (also called NEMO). The amino-terminal a-helical region of NEMO has been shown to interact with the C-terminal segment of IKKα and IKKβ. A small peptide from the C-terminus of IKKα and IKKβ NEMO has been shown to block this interaction. To make it cell permeable, the NBD peptide was conjugated to a small sequence from the antennapedia homeodomain. This peptide has been shown to specifically suppress NF-κB activation. The peptide without the antennapedia homeodomain protein sequence was used as a control.

Results disclosed above have shown that curcumin suppressed constitutive NF-κB which in turn led to suppression of cell proliferation and induction of apoptosis. Here the NBD and control peptide was used to establish that NF-κB suppression is linked to proliferation and apoptosis.

Figure 8A:
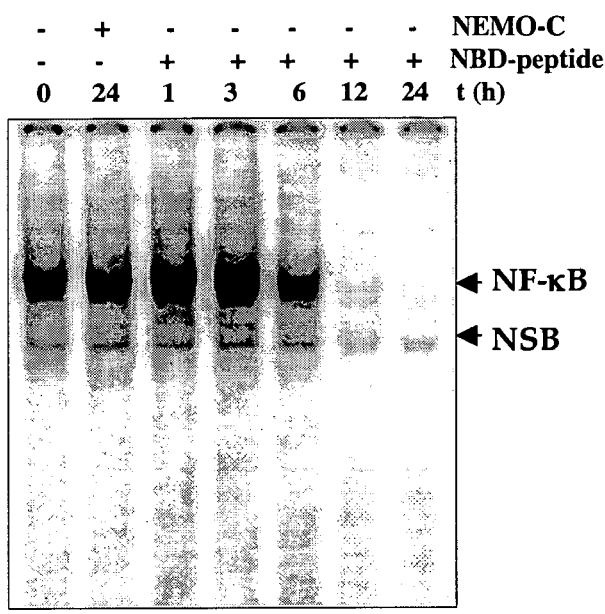
FIG. 8A: U266 cells ($2\times10^6$ cells/ml) were treated with indicated concentrations of NEMO-control or NBD-peptide (100 μM) for the indicated times. Nuclear extracts were then checked for the presence of NF-κB DNA-binding activity by EMSA.
Figure 8C:
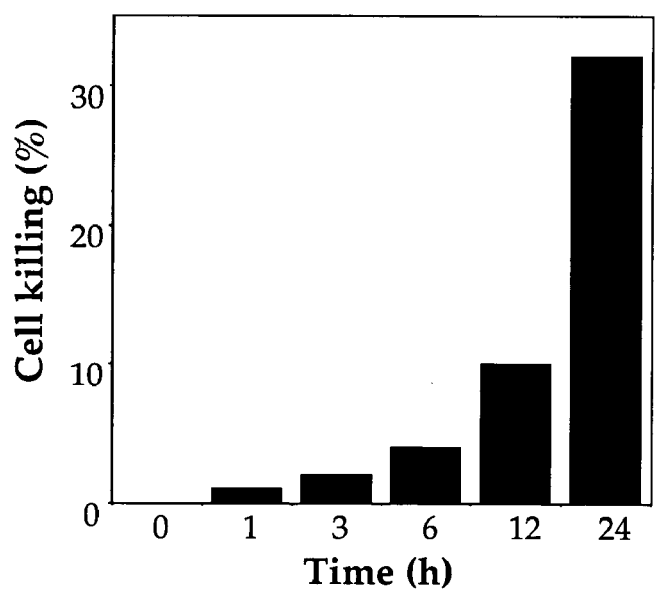
FIG. 8C: U266 cells ($2\times10^6$ cells/ml) were treated with indicated concentrations of NEMO-control or NBD-peptide (100 μM) for the indicated time periods, and cell viability was monitored by the trypan blue dye exclusion method. Percent cell killing was determined as: (number of trypan blue stained cells/total cells)×100.
Figure 8B:
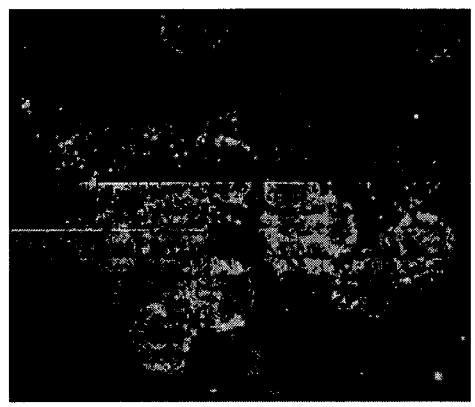
FIG. 8B: Untreated or NBD-peptide-treated (100 μM; 12 h) U266 cells were cytospun, and p65 immunocytochemistry was performed as described. Red stain indicates the localization of p65 and blue stain indicates nucleus (magnification 200×).
Figure 8B:
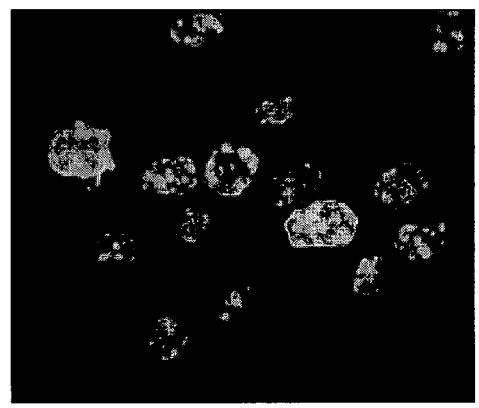
Figure 8B:
Figure 8B:

As shown in FIG. 8A, treatment of U266 cells with NEMO-control peptide had no effect, whereas NBD peptide suppressed constitutive NF-kB in a time-dependent manner with complete suppression occurring at 12 h. Suppression of NF-kB activation in multiple myeloma cells was also confirmed independently by immunocytochemistry. The results indicated a decrease in the nuclear pool of the p65 subunit of NF-κB (FIG. 8B). Suppression of NF-κB by NBD peptide also led to inhibition of cell proliferation of U266 cells. Approximately 32% suppression of cell growth was observed after 24 h of NBD treatment (FIG. 8C). These results thus indicate that NF-κB suppression is indeed linked to antiproliferative effects in multiple myeloma cells.

EXAMPLE 17

Curcumin Potentiates the Cytotoxic Effects of Vincristine

Figure 9:
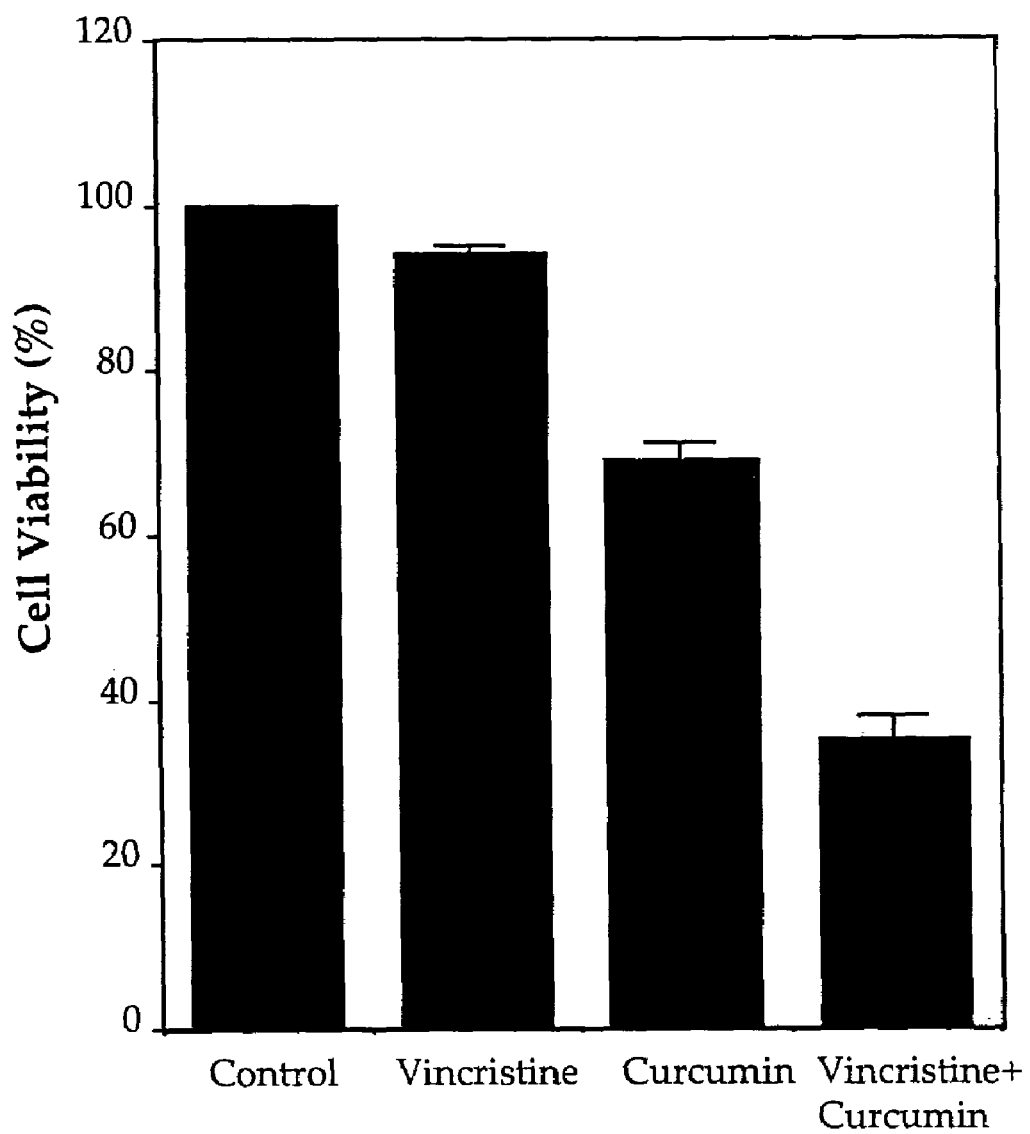
FIG. 9 shows that curcumin potentiates the cytotoxic effect of vincristine in multiple myeloma cells. U266 cells (10000 cells/0.1 ml) were incubated without or with vincristine (50 μM) in the absence or presence of curcumin (10 μM) for 24 h, and then cell viability was determined by the MTT method.

Because NF-κB has been implicated in chemoresistance of cells, the effects of curcumin on chemosensitivity was investigated. Vincristine was chosen because it is one of the chemotherapeutic agents used for the treatment of multiple myeloma. Treatment of U266 cells with vincristine in the presence of low concentrations of curcumin (10 μM) decreased cell viability after 24 h (FIG. 9). The highest concentration (50 μM) of vincristine alone was minimally effective in killing U266 cells; curcumin alone killed approximately 35% of the cells; whereas the two agents together killed 65% of the cells. These results indicate that curcumin may sensitize multiple myeloma cells to the cell killing effects of vincristine.

EXAMPLE 18

NF-κB is Constitutively Active in CD138+ Cells from Multiple Myeloma Patients

This example examined whether NF-κB and STAT3 are constitutively active in fresh cells from multiple myeloma patients. Table 1 describes the clinical characterization of these patients. PBMC from normal subjects were used as a control.

CD138+ plasma cells from bone marrow of multiple myeloma patients were isolated as follows. CD138 antigen, also known as Syndecan-1, is expressed on normal and malignant plasma cells, but not on circulating B cells, T cells, and monocytes. Anti-CD138 microbeads (Miltenyi Biotec, Auburen, Calif.) were used for positive selection of CD138+ cells from bone marrow derived from multiple myeloma patients. Two to 10 ml bone marrow sample was aspirated from the upper iliac crest or sternum and diluted in an equal volume of HEPES-buffered cell culture medium, IMDM, supplemented with heparin at a concentration of 100 U/ml, and mixed gently. To prevent the cells from clumping, the dilute marrow was suspended in IMDM containing 100 U deoxyribonuclease (Dnase) I/ml and shaken gently at room temperature for an additional 30 min. Next, 30 ml of dilute bone marrow cell suspension was layered over 20 ml of Ficoll-Paque in 50 ml conical tubes and spun at 400×g for 30 min to isolate mononuclear cells (MNC). Thereafter, the MNC layer at the interface were harvested and washed twice with PBS containing 2 mM EDTA for 10 min at 300×g at room temperature.

The MNC concentration was adjusted to $10^7$ per 80 μl of Running buffer (PBS with 2 mM EDTA plus 0.5 mM BSA). For every $10^7$ MNC in 80 μl of running buffer, 20 μl of anti-CD138 microbeads (Miltenyi Biotec, Auburen, Calif.) were added and the cell suspension was incubated at 4° C.–8° C. for 15 min. The cell suspension was then diluted with 1 ml of cold Running buffer and centrifuged at 300×g for 10 min at 4° C. The supernatant was discarded, and the cell pellet was suspended in 1 ml Running buffer, and loaded onto the magnetic column of the AutoMACS system (Miltenyi Biotec) placed in a laminar flow hood.

Anti-CD138+ cells were isolated by positive selection. The purity of the isolated CD138+ plasma cell population was determined by treating $10^5$ CD138+ cells with 10 μl of anti-CD138 conjugated with phycoerythrin (PE) and incubated in the dark in the refrigerator at 6° C.–12° C. The cells were washed twice with cold PBS, fixed with 1% paraformaldehyde, and analyzed using a FACSCalibur flow cytometer (Becton Dickinson, San Jose, Calif.).

Figure 10A:
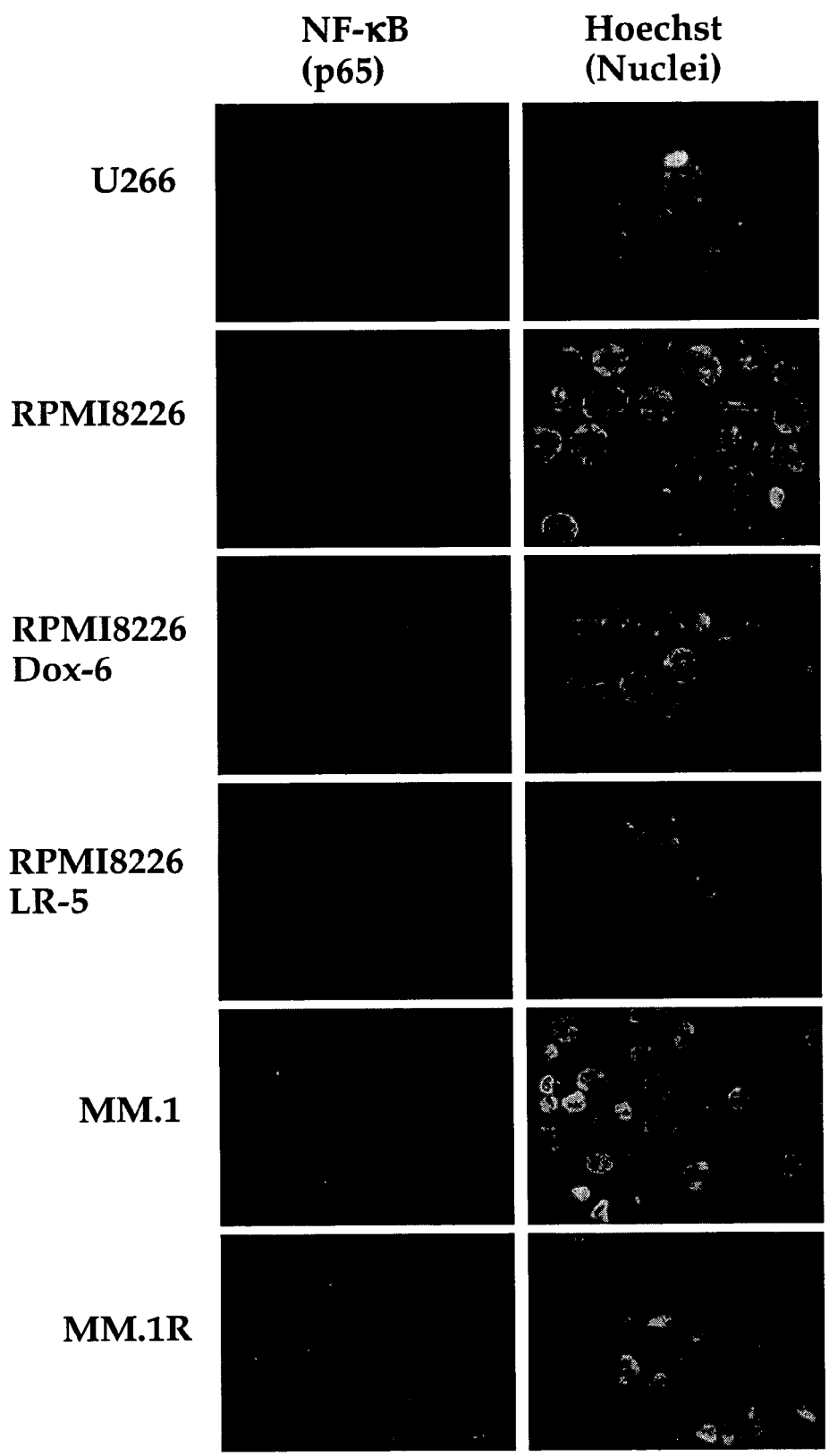
FIG. 10 shows immunocytochemical localization of NF-κB in human multiple myeloma cell lines (FIG. 10A), peripheral blood mononuclear cells (PBMC) from healthy subjects, and bone marrow CD138$^+$ multiple myeloma cells from a patient (FIG. 10B). PBMC were collected from the blood of a healthy subject by Ficoll-Paque density gradient centrifugation. CD138$^+$ cells were enriched from bone marrow aspirates of multiple myeloma patient (patient #1), enriched by magnetic bead separation method, and immunostained for NF-κB (p65). Red stain indicates specific staining for NF-κB, whereas blue stain indicates the relative position of the nuclei in the corresponding view.
Figure 10B:
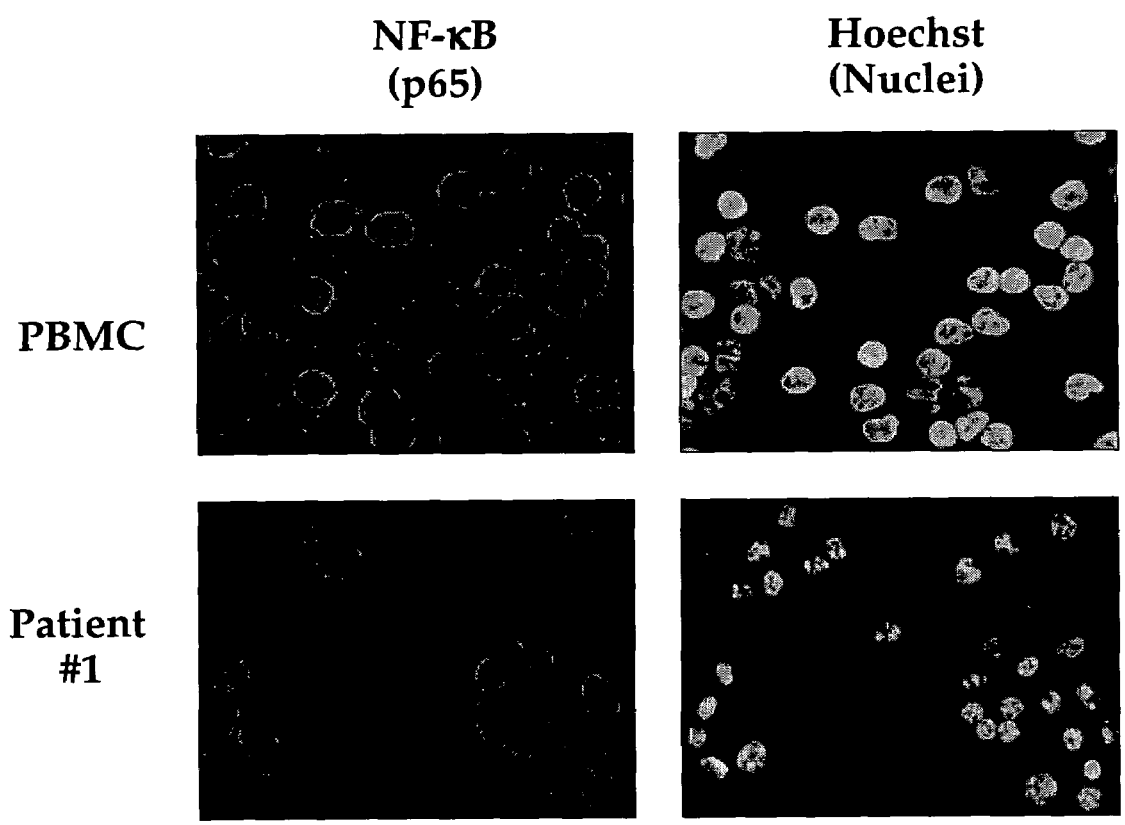

The NF-κB status of various multiple myeloma cell lines was examined first. FIG. 10A indicates all the multiple myeloma cell lines expressed the nuclear form of NF-κB, indicating that multiple myeloma cell lines express the constitutively active form of NF-κB. PBMC (the control) expressed the cytoplasmic (inactive) form of NF-κB (FIG. 10B, upper panel). Multiple myeloma cells from patient #1, like multiple myeloma cell lines, expressed only the nuclear form of NF-κB (FIG. 10B, lower panel).

Figure 11A:
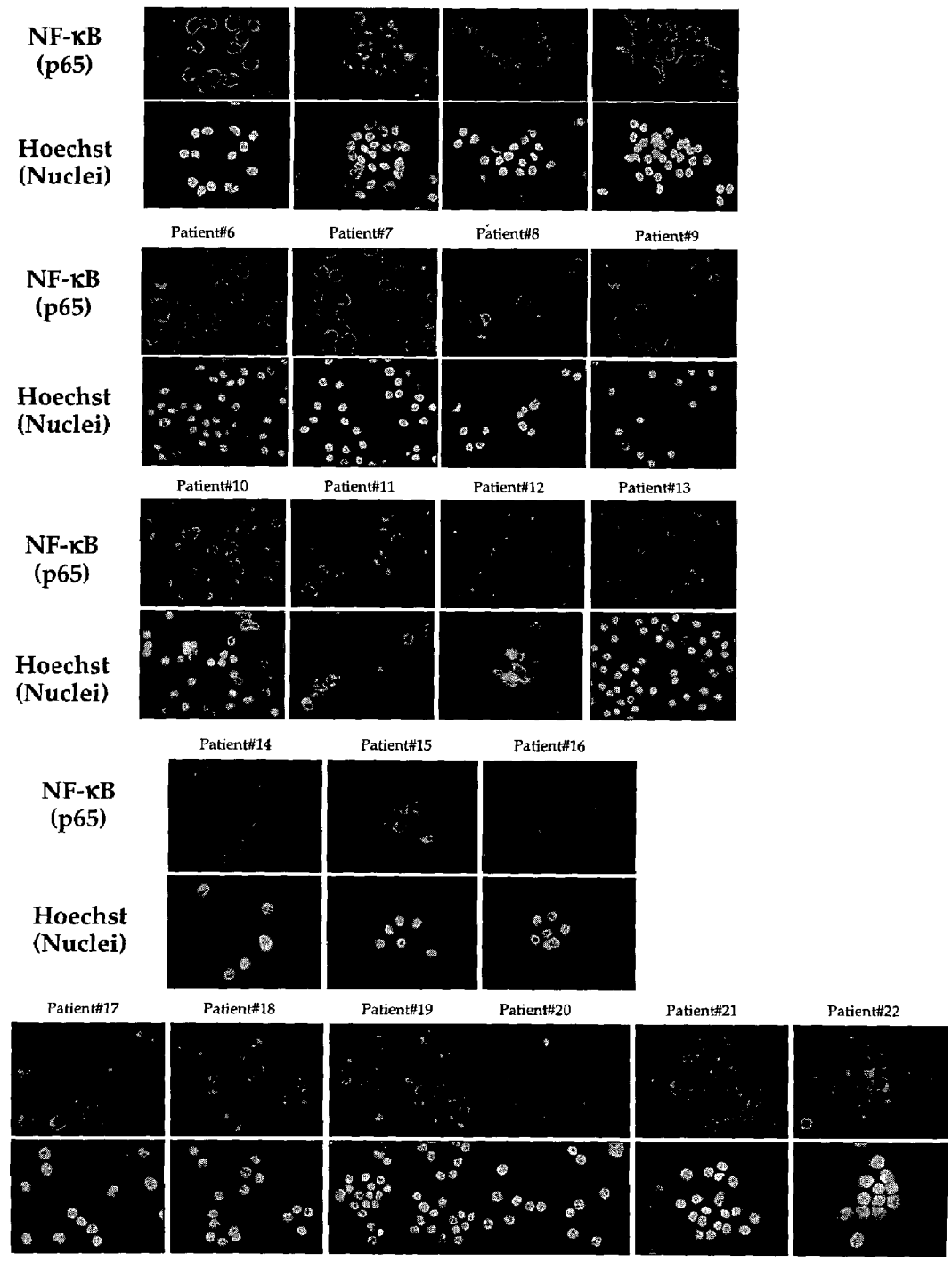
FIG. 11 shows nuclear localization of NF-κB in bone marrow CD138+ cells from multiple myeloma patients. Enriched CD138+ cells from bone marrow aspirates of different multiple myeloma patients were immunostained for NF-κB (p65) (FIG. 11A). Red stain indicates specific staining for NF-κB, whereas blue stain indicates a relative position of the nuclei in the corresponding view.
FIG. 11B shows enriched CD138+ cells ($2\times10^6$ cells) from bone marrow aspirates of a multiple myeloma patient (patient #4) were tested for NF-κB activity in the nuclei by electrophoretic mobility shift assay. Untreated or TNF-treated KBM-5 (TNF-1 nM, 30 min) was used as negative and positive controls respectively.

Twenty-two different multiple myeloma patient samples were then examined for NF-κB activation by the method described above. All 22 patients showed expression of NF-κB protein (p65) in the nucleus, indicating constitutive activation (FIG. 11). The extent of activation, however, was quite variable. Three patients showed low, five showed moderate and 14 showed high expression of constitutive NF-κB.

Figure 11B:
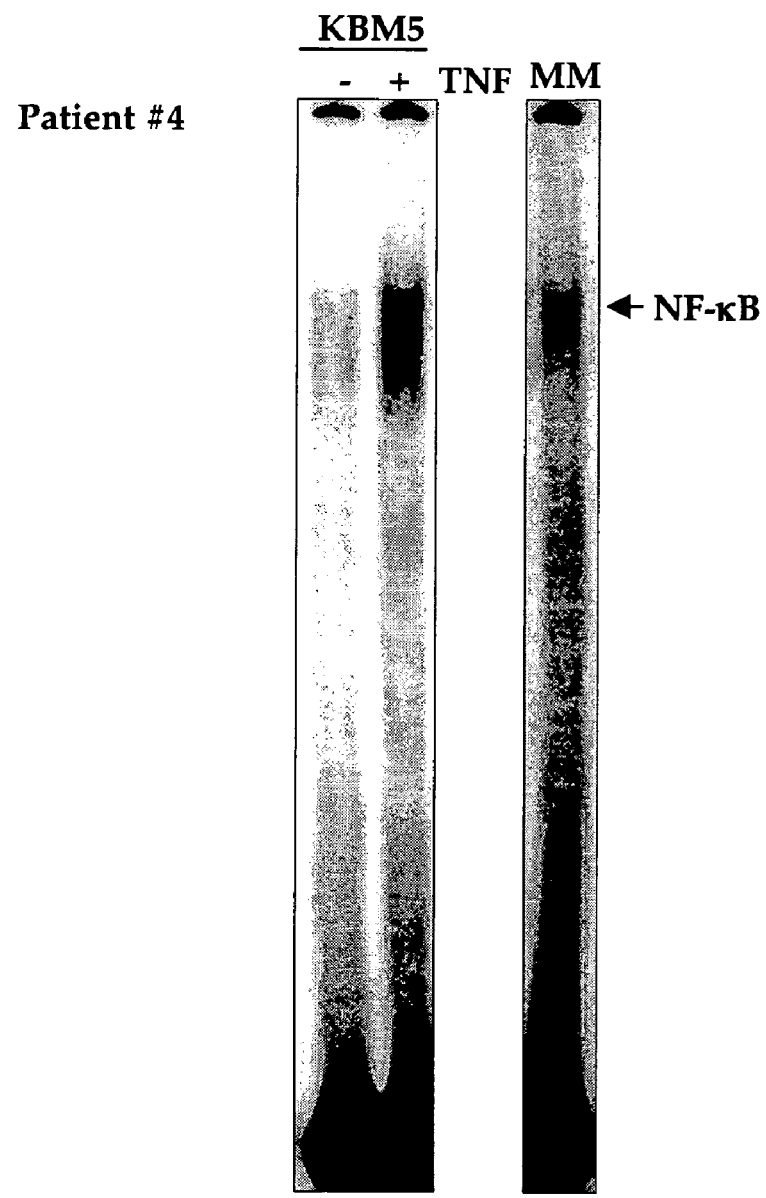
Figure 12A:
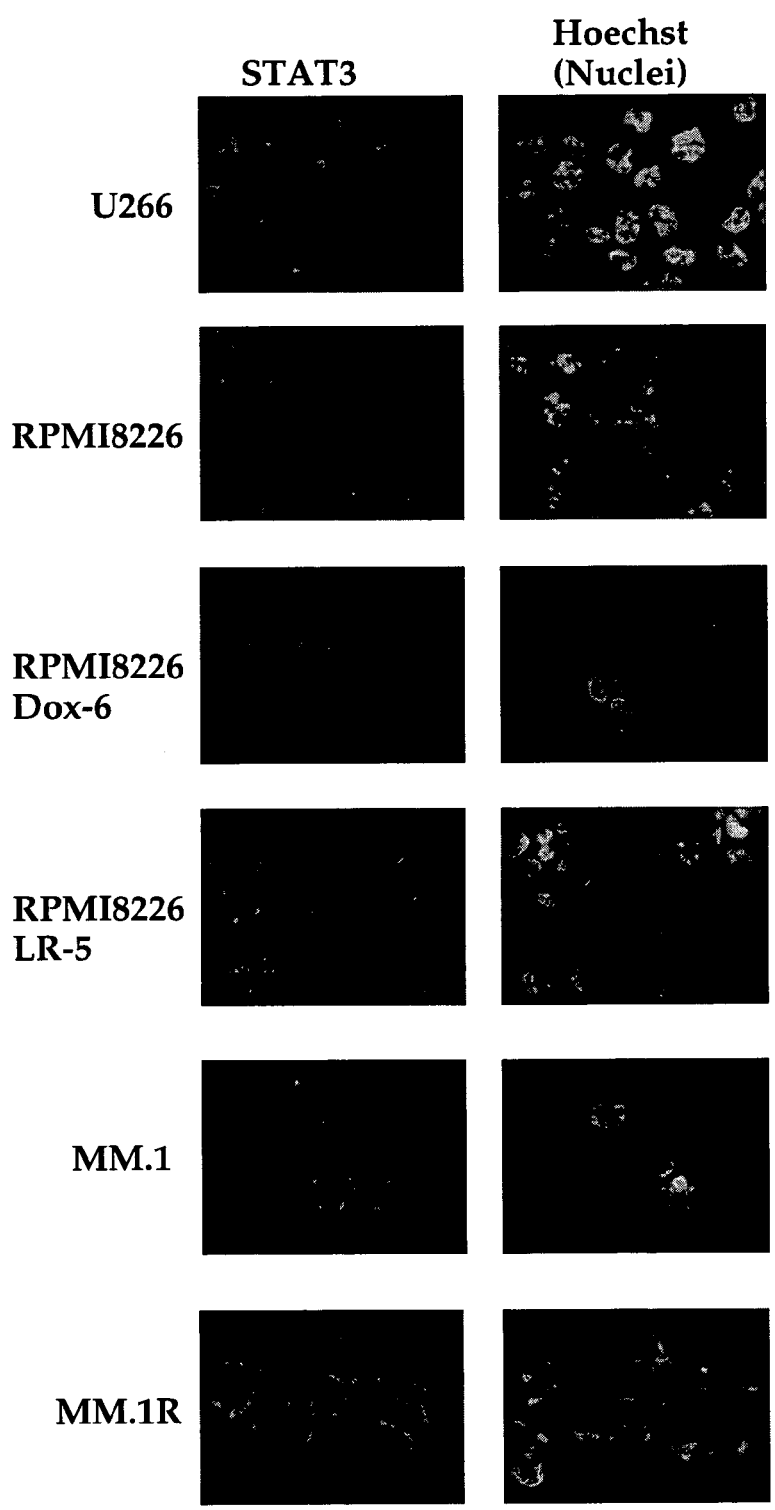
FIG. 12 shows nuclear localization of STAT3 in multiple myeloma cell lines (FIG. 12A), PBMCs and bone marrow CD138+ multiple myeloma cells from patients (FIGS. 12B–C). Enriched CD138+ cells from bone marrow aspirates of different multiple myeloma patients were immunostained for STAT3 as described below. Red stain indicates specific staining for STAT3, whereas blue stain indicates the relative position of the nuclei in the corresponding view.
Figure 12B:
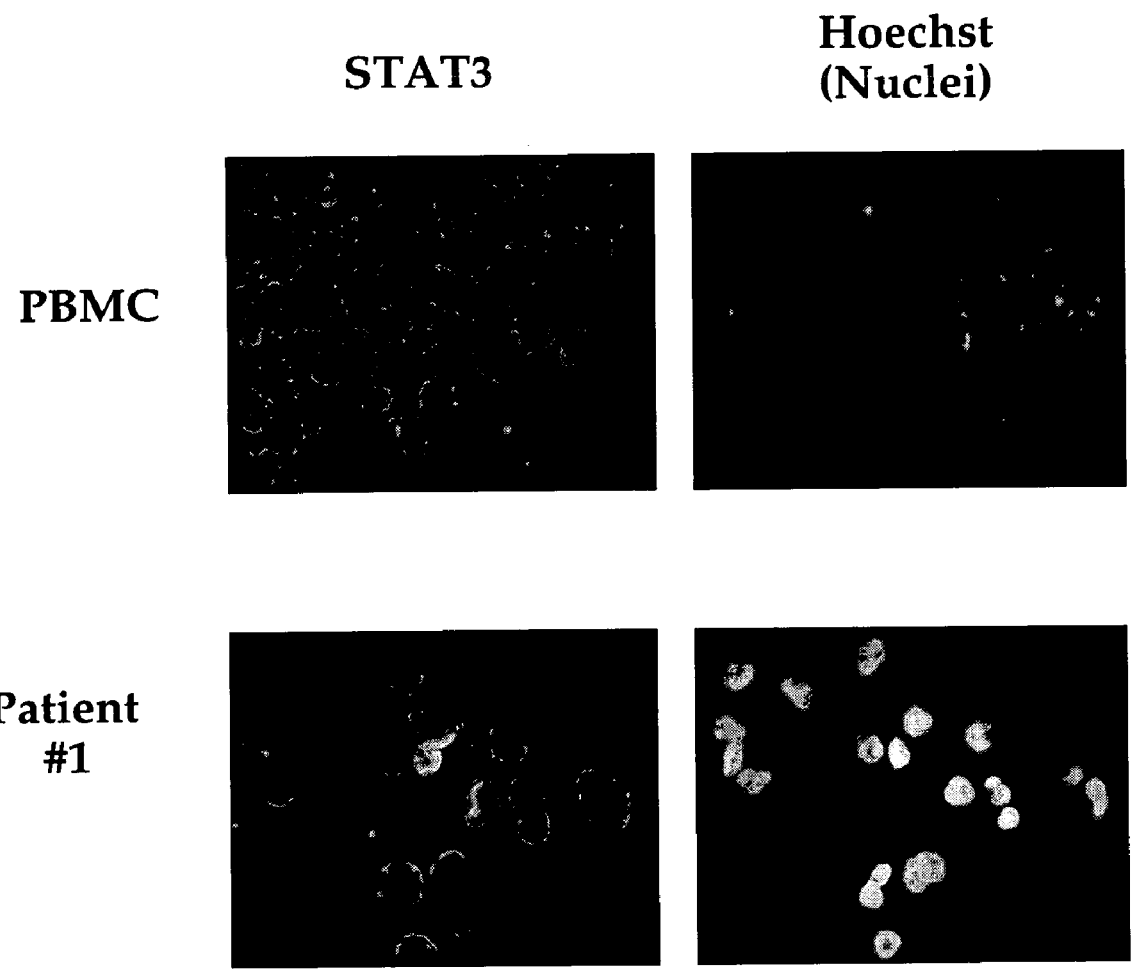
Figure 12C:
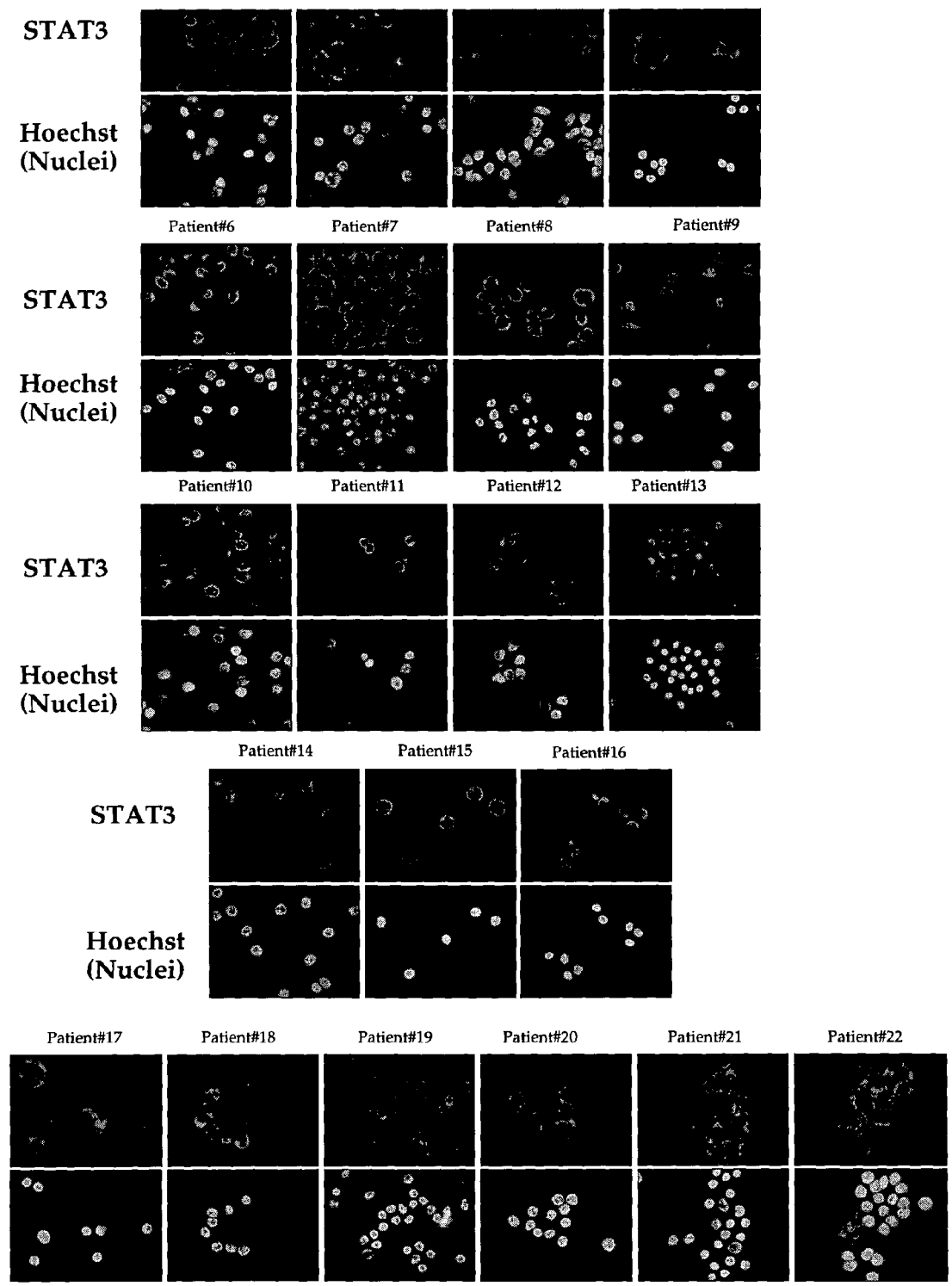

The constitutive activation of NF-κB was independently confirmed by the electrophoretic mobility shift assay. As shown in FIG. 11B, control NF-κB in KBM-5, a myeloid cell line which has no constitutive NF-κB, was activated by TNF. Similarly, NF-κB activation was also found in the sample from patient #4, which showed constitutive NF-κB activation by immunocytochemistry (FIG. 11B).

nucleus (FIG. 12C). The extent of nuclear STAT3 also varied. One patient had none, three had low, five had moderate, and 14 patients showed high expression of constitutive STAT3 activation.

TABLE 1

Clinical Characteristics of Multiple Myeloma Patients

| Patient # | Age, Sex | MM Type | Hgb | WBC | Platelets (1000) | % Plasma cells | Serum Paraproteins (gm) | Urine Paraproteins (gm) | Site |
|---|---|---|---|---|---|---|---|---|---|
| 1 | 67 M | IgG | 10.3 | 4.2 | 203 | 44 | 6.4 | 0.6 | Bone (diffuse) |
| 2 | 40 F | IgG | 8.6 | 5.0 | 49 | 90 | 9.3 | 3.4 | (−) bone survey |
| 3 | 57 F | IgG | 10.2 | 5.3 | 217 | 90 | 6.7 | 4.25 | Bone (diffuse) |
| 4 | 50 M | IgA | 11.1 | 4.9 | 184 | 40 | 5.7 | 0 | Bone (diffuse) |
| 5 | 52 M | IgG | 12.1 | 2.9 | 257 | 35 | 4.4 | 0.12 | (−) bone survey |
| 6 | 56 F | IgG | 8 | 4.0 | 33 | 96 | 8.4 | 1.68 | (−) bone survey |
| 7 | 63 F | IgG | 10 | 5.5 | 336 | 45 | 9.9 | 0.36 | (−) bone survey |
| 8 | 63 M | IgG | 12.3 | 4.6 | 151 | 18 | (−) | 0.02 | Bone (diffuse) |
| 9 | 64 M | IgG | 10.5 | 4.2 | 219 | 50 | 3.5 | 0.01 | T11, Clavicle |
| 10 | 35 F | IgA | 9.1 | 2.6 | 85 | 7 | 1.5 | 0.21 | (−) bone survey |
| 11 | 52 M | IgA | 10.4 | 3.3 | 54 | 66 | 0.8 | 17 | (−) bone survey |
| 12 | 45 M | IgG | 10.2 | 11.8 | 338 | 63 | 0.1 | 4.273 | Bone (diffuse) |
| 13 | 54 M | IgG | 14.1 | 4.5 | 262 | 14 | 4.7 | 0 | (−) bone survey |
| 14 | 66 M | IgA | 10.2 | 5.9 | 154 | 60 | 3.4 | 0.1 | Bone (diffuse) |
| 15 | 50 F | IgG | 11.9 | 7.1 | 364 | 18 | 3.7 | 0 | Bone (diffuse) |
| 16 | 40 F | IgG | 10.3 | 6.2 | 335 | 60 | (−) | 0 | Skull, Apex |
| 17 | 58 M | IgA | 13.9 | 5.1 | 205 | 20 | 4.3 | 0 | (−) bone survey |
| 18 | 67 M | IgG | 8.9 | 8.8 | 52 | 25 | 0.4 | 3.9 | (−) bone survey |
| 19 | 56 M | IgG | 13.3 | 7.8 | 233 | 22 | 4.6 | 0.02 | Ribs |
| 20 | 65 M | IgG | 13.3 | 4.8 | 227 | 40 | 2.8 | 0.32 | C2 |
| 21 | 57 M | IgA | 6.0 | 9.6 | 219 | 68 | 3.1 | 4.8 | (−) bone survey |
| 22 | 67 F | IgG | 12.8 | 5.0 | 249 | 14 | 1.6 | 0 | (−) bone survey |

MM, multiple myeloma;
Hgb; hemoglobin;
WBC, white blood cells.

EXAMPLE 19

STAT3 is Constitutively Active in CD138+ Cells from Multiple Myeloma Patients

Only U266 cells expressed STAT3 in nuclei (FIG. 12A), suggesting that U266 cells express the constitutively active form of STAT3. PBMC from normal subjects expressed the cytoplasmic (inactive) form of STAT3 (FIG. 12B, upper panel). Multiple myeloma cells from patient #1 likewise expressed the nuclear form of STAT3. This suggests that fresh cells from this patient express constitutively active form of STAT3 (FIG. 12B, lower panel).

The status of STAT3 activation was examined in CD138+ cells from 22 multiple myeloma patients. Unlike NF-κB, not all patients showed expression of STAT3 protein in the

EXAMPLE 20

Curcumin Downregulates Constitutive NF-κB and STAT3 Activation in CD138+ Cells from Multiple Myeloma Patients:

Results presented above indicate that CD138+ cells from most multiple myeloma patients expressed constitutively active NF-κB and STAT3. This example investigated whether curcumin suppressed the constitutive activation of NF-κB and STAT3 in fresh cells from multiple myeloma patients. To determine this, CD138+ cells from multiple myeloma patients were exposed to 50 μM curcumin for 2 h and then examined for STAT3 and NF-κB expression.

Figure 13A:
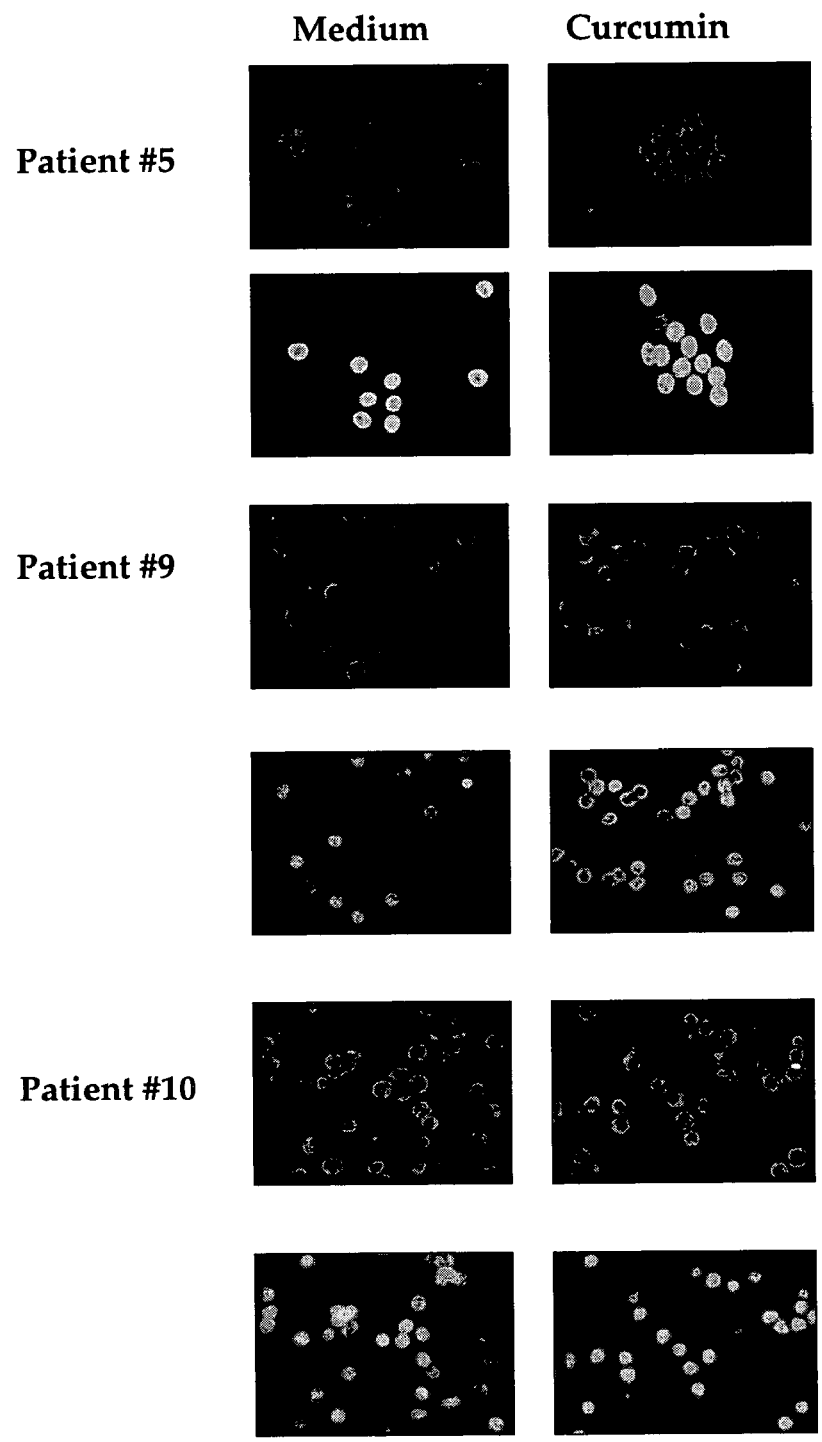
FIG. 13 shows curcumin prevents nuclear localization of NF-κB and STAT3 in bone marrow CD138+ multiple myeloma cells. Enriched CD138+ cells ($1\times10^5$ cells/0.1 ml) from bone marrow aspirates of multiple myeloma patients #5, #9, or #10 were cultured in the absence or presence of curcumin (50 μM) for 1 h for STAT3 analysis or for 2 h for NF-κB analysis. The cells were fixed on slides by cytospin centrifugation and immuno-stained for NF-κB or STAT3. Red stain indicates specific staining for NF-κB or STAT3, whereas blue stain indicates the relative position of the nuclei in the corresponding view.
Figure 13B:
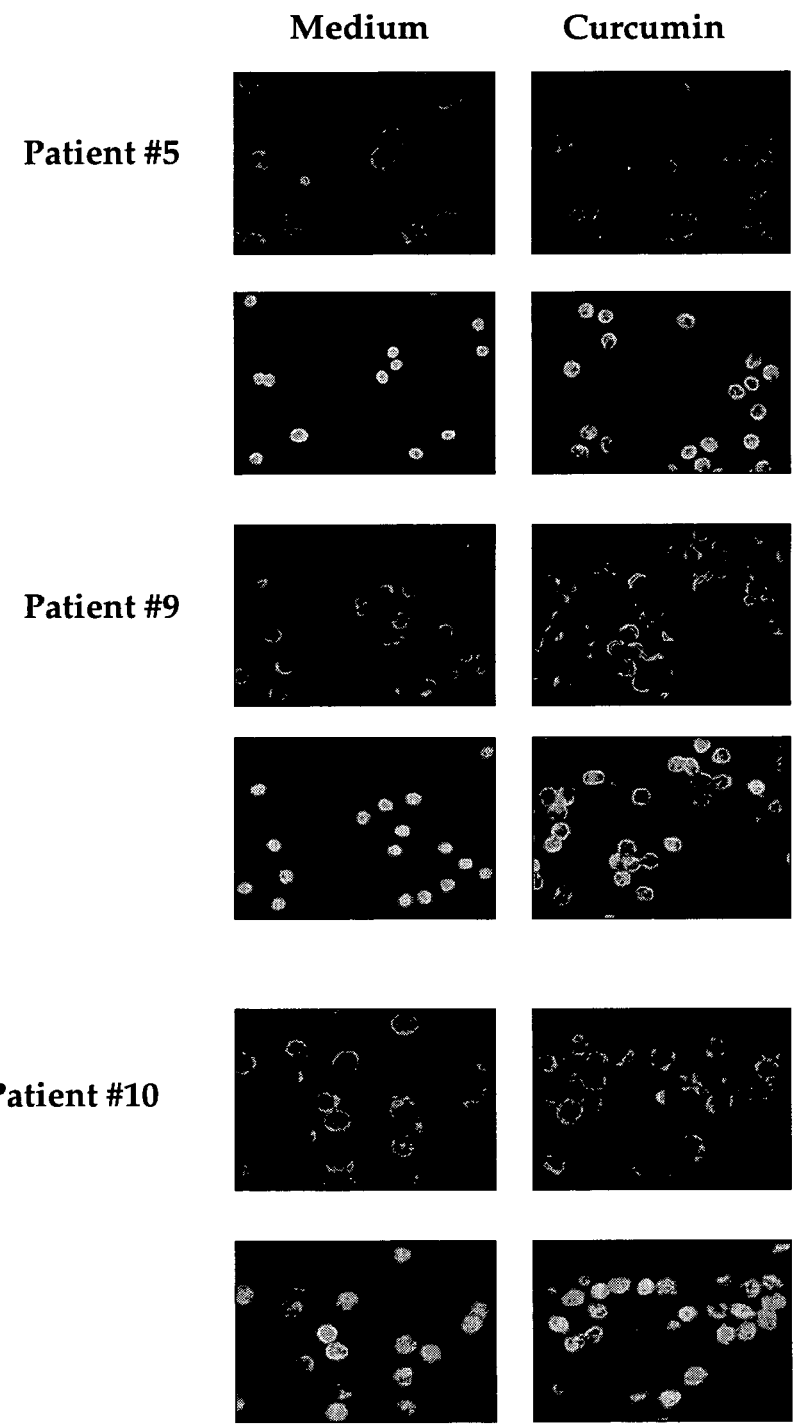
Figure 14A:
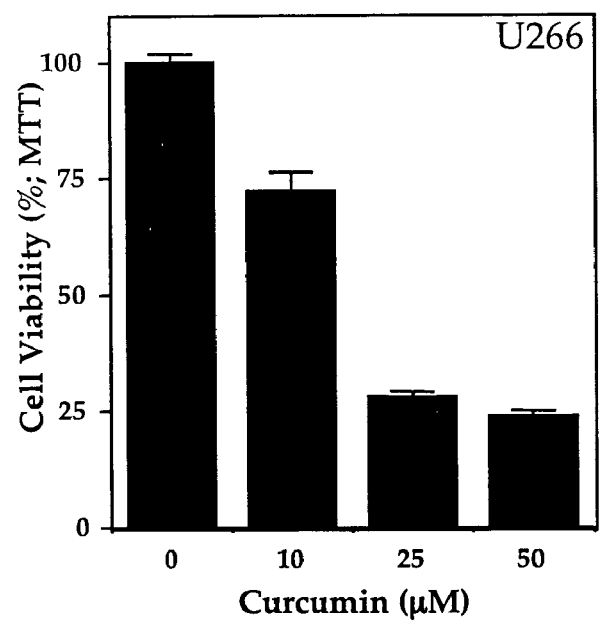
FIG. 14 shows curcumin inhibits the growth/viability of human multiple myeloma cell line U266 and bone marrow CD138+ multiple myeloma cells. Cell line U266 (FIG. 14A) or enriched CD138+ cells ($2\times10^4$ cells/0.1 ml) from bone marrow aspirates of multiple myeloma patients #7, #9, or #10 (FIGS. 14B–D) were cultured in the absence or presence of the indicated concentrations of curcumin for 24 h and cell viability was measured by MTT assay (FIGS. 14A, B) or standard Trypan blue dye exclusion method (FIGS. 14C, D).
Figure 14B:
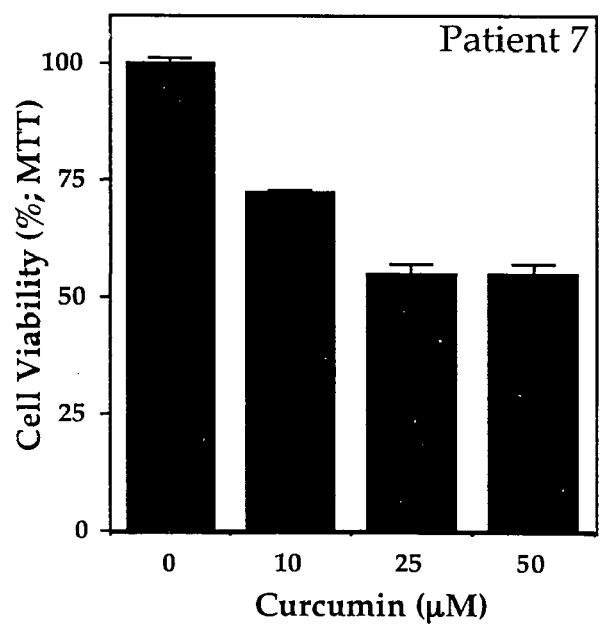
Figure 14C:
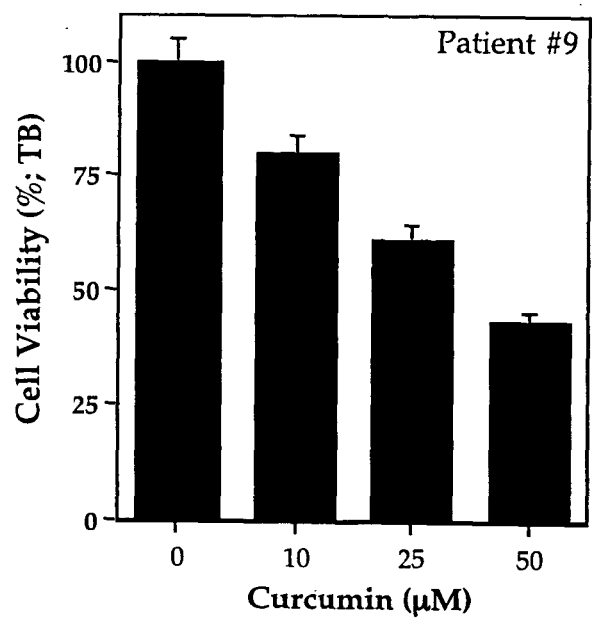
Figure 14D:
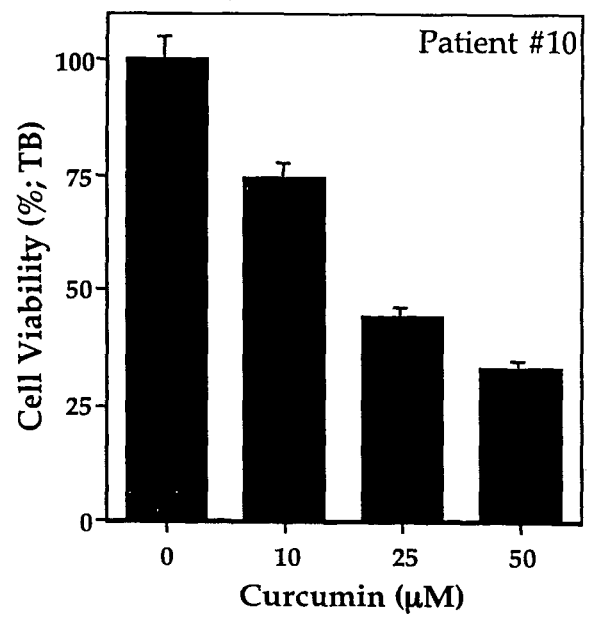

FIG. 13A indicates that NF-κB was constitutively active in patient #5, #9 and #10 (the only patients tested) and exposure to curcumin downregulated NF-κB. Results in FIG. 13B indicate that STAT3 was likewise constitutively active in patient #5, #9 and #10, and exposure to curcumin downregulated this transcripion factor.

EXAMPLE 21

Curcumin Downregulates the Survival of CD138+ Cells from Multiple Myeloma Patients Because NF-κB and STAT3 activation have been implicated in cell survival, and curcumin downregulated these transcription factors in CD138+ cells from multiple myeloma patients, it is of interest to investigate whether this downregulation leads to a decrease in cell viability. Cells were exposed to different concentrations of curcumin and then examined for cell viability by the MTT method. As shown in FIG. 14, curcumin treatment of U266 cells or fresh cells from patients #7, #9 and #10 decreased cell survival in a dose-dependent manner. Results in FIG. 14B indicate that STAT3 was also constitutively active in patient #5, #9 and #10 and that exposure to curcumin downregulated this transcripion factor. These results suggest that constitutive activation of NF-κB and STAT3 are cell survival factor for CD138+ cells from multiple myeloma patients.

EXAMPLE 22

Figure 15A:
FIG. 15 shows the effect of curcumin and dexamethasone on nuclear localization of NF-κB and STAT3 in bone marrow CD138+ multiple myeloma cells. Enriched CD138+ cells ($1\times10^5$ cells/0.1 ml) from bone marrow aspirates of multiple myeloma patient #20 were cultured in the absence or presence of curcumin or dexamethasone (50 μM each) for 2 h, and cells were fixed on slides by cytospin centrifugation and immunostained for NF-κB or STAT3. Red stain indicates the specific staining for NF-κB or STAT3 as indicated, whereas blue stain indicates the relative position of the nuclei in the corresponding view.
Figure 15A:
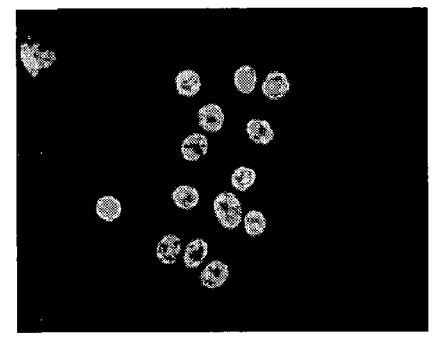
Figure 15A:
Figure 15A:
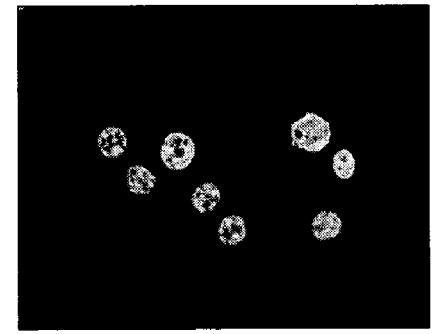
Figure 15A:
Figure 15A:
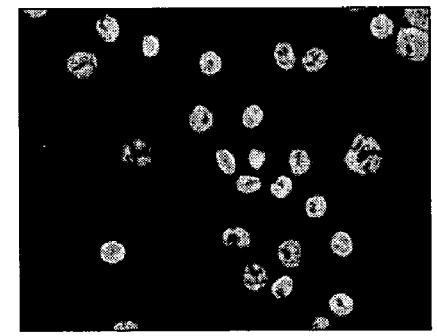
Figure 15B:
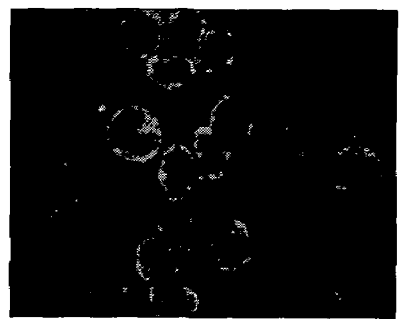
Figure 15B:
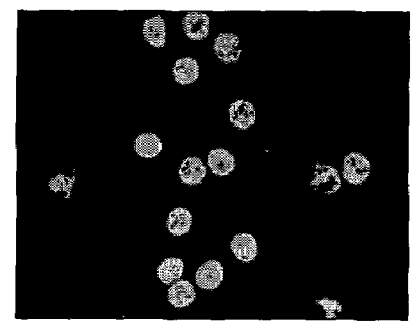
Figure 15B:
Figure 15B:
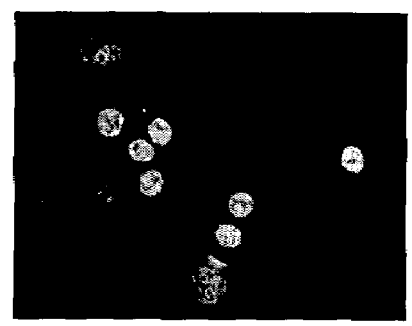
Figure 15B:
Figure 15B:
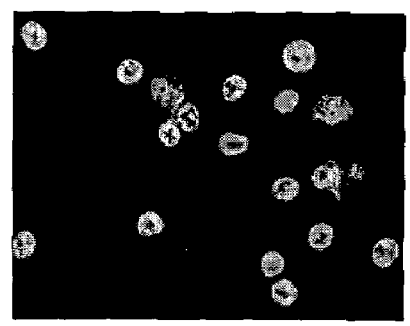

Dexamethasone Downregulates Constitutive NF-κB and STAT3 Activation in CD138+ Cells from Multiple Myeloma Patients Currently, dexamethsone is used as a standard therapy of multiple myeloma patients. Whether dexamthesaone also affects NF-κB and STAT3 in cells from multiple myeloma patients was investigated. Results in FIG. 15 indicate that dexamthasone downregulated the constitutitve activation of both NF-κB (FIG. 15A) and STAT3 (FIG. 15B) in CD138+ cells from patient #20. Dexamthasone was, however, less effective than curcumin in downregulation of either transcription factor.

Figure 16A:
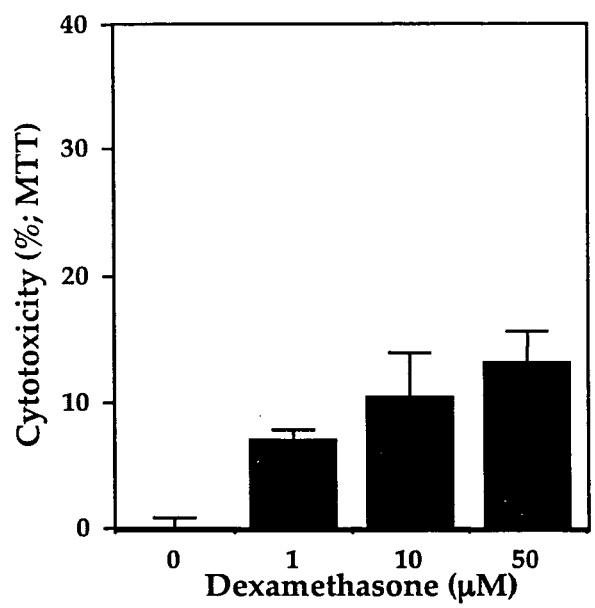
FIG. 16 shows the effect of curcumin and dexamethasone on growth/viability of bone marrow CD138+ multiple myeloma cells. Enriched CD138+ cells ($2\times10^5$ cells/0.1 ml) from bone marrow aspirates of multiple myeloma patient #20 were cultured in the absence or presence of indicated concentrations of curcumin (FIG. 16A) or dexamethasone (FIG. 16B) for 24 h, and cell viability was measured by MTT assay.
Figure 16B:
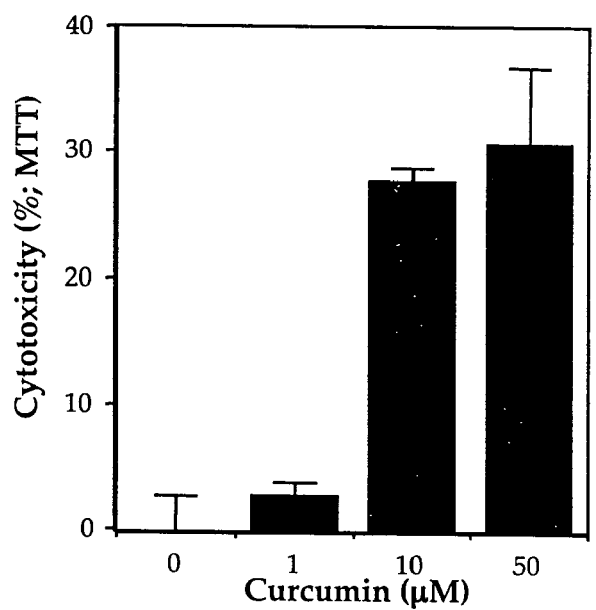

Dexamethasone also affects survival of cells from multiple myeloma patients. Results in FIG. 16A indicate that dexamethasone decreased the survival of cells from patient #20. Dexamthasone, however, was much less effective than curcumin (FIG. 16B).

That dexamthasone can suppress NF-κB activation has been previously reported. The present study is the first to show the effect of dexamethasone on STAT3. Curcumin was much more effective in inhibiting the survival of multiple myeloma cells than dexamethasone (FIG. 16). Because of the established pharmacological safety of curcumin and its ability to downregulate expression of large number of genes involved in cell survival and chemoresistance, it provides sufficient rationale to combine curcumin with dexamethasone for the treatment of multiple myeloma patients. Recently, a proteosomal inhibitor (PS341, called Velcade) and an inhibitor of TNF production (thalidomide) have been approved for the treatment of multiple myeloma patients. Both of these inhibitors have also been shown to suppress NF-κB activation. The results presented herein suggest that NF-κB and STAT3 are ideal targets for drug development for the treatment of multiple myeloma.

The following references were cited herein:

Bharti et al., Curcumin (diferuloylmethane) down-regulates the constitutive activation of nuclear factor-k B and IkBa kinase in human multiple myeloma cells, leading to suppression of proliferation and induction of apoptosis. Blood 101:1053 (2003).

Chaturvedi et al., Assay for redox-sensitive transcription factor.

Methods Enzymol. 319:585–602 (2000).

Chaturvedi et al., Tumor necrosis factor and lymphotoxin. Qualitative and quantitative differences in the mediation of early and late cellular response. J Biol. Chem. 269: 14575 (1994).

Cheng et al., Phase I chemoprevention clinical trail of curcumin. Proc. Am. Soc. Clin. Oncol. 17:558a (1998).

Kawamori et al., Chemopreventive effect of curcumin, a naturally occurring anti-inflammatory agent, during the promotion/progression stages of colon cancer. Cancer Res. 59:597–601 (1999).

Manna et al., Leflunomide suppresses TNF-induced cellular responses: effects on NF-kappa B, activator protein-1, c-Jun N-terminal protein kinase, and apoptosis. J Immunol. 165:5962–5969 (2000).

Manna et al., Overexpression of manganese superoxide dismutase suppresses tumor necrosis factor-induced apoptosis and activation of nuclear transcription factor-kappaB and activated protein-1. J Biol Chem. 273:13245–13254 (1998).

Rao et al., Chemoprevention of colon carcinogenesis by dietary curcumin, a naturally occurring plant phenolic compound. Cancer Res. 55:259–266 (1995).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of inhibiting proliferation of multiple myeloma cells in vitro or in vivo, comprising the steps of: contacting said cells with an amount of a curcuminoid effective to inhibit the proliferation of multiple myeloma cells.

2. A method of inducing apoptosis in multiple myeloma cells in vitro or in vivo, comprising the steps of: contacting said cells with an amount of a curcuminoid effective to induce apoptosis in multiple myeloma cells.

3. A method of increasing the cytotoxic effects of one or more chemotherapeutic agents against multiple myeloma cells, comprising the steps of: contacting said cells with said one or more chemotherapeutic agents and a curcuminoid, wherein said curcuminoid increases the cytotoxic effects of said one or more chemotherapeutic agent against multiple myeloma cells.

4. The method of claim 3, wherein said one or more chemotherapeutic agent is selected from the group consisting of vincristine, BCNU, melphalan, cyclophosphamide, Adriamycin, prednisone, velcade, thalidomide, and dexamethasone.

5. The method of claim 3, wherein said multiple myeloma cells are CD138.sup.+ plasma cells.

6. A method of treating multiple myeloma in an individual, comprising the step of administering a therapeutically effective amount of a curcuminoid to said individual.

7. The method of claim 6, wherein said curcuminoid is administered orally.

8. The method of claim 6, wherein said curcuminoid is administered in a dose of from about 0.01 mg/kg of the individual's body weight to about 500 mg/kg of the individual's body weight.

9. A method of increasing the cytotoxic effects of one or more chemotherapeutic agents against multiple myeloma cells in an individual, comprising the steps of: administering to said individual said one or more chemotherapeutic agents and a curcuminoid, wherein said curcuminoid increases the cytotoxic effects of said one or more chemotherapeutic agents against multiple myeloma cells in said individual.

10. The method of claim 9, wherein said one or more chemotherapeutic agents is selected from the group consisting of vincristine, BCNU, melphalan, cyclophosphamide, Adriamycin, prednisone velcade, thalidomide, and dexamethasone.

11. The method of claim 9, wherein said curcuminoid is administered orally.

12. The method of claim 9, wherein said curcuminoid is administered in a dose of from about 0.01 mg/kg of the individual's body weight to about 500 mg/kg of the individual's body weight.

13. The method of claim 9, wherein said multiple myeloma cells are CD138.sup.+ plasma cells.

* * * * *

UNITED STATES PATENT AND TRADEMARK OFFICE
CERTIFICATE OF CORRECTION

PATENT NO. : 7,196,105 B2 Page 1 of 1
APPLICATION NO. : 10/602303
DATED : March 27, 2007
INVENTOR(S) : Aggarwal It is certified that error appears in the above-identified patent and that said Letters Patent is hereby corrected as shown below:

In claim 4, column 21, line 67, delete "agent" and insert --agents-- therefor.

In claim 10, column 23, line 6, after "prednisone", insert --, --therefor.

Signed and Sealed this

Fifteenth Day of May, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 9
<212> TYPE: DNA
<213> ORGANISM: Unknown
<220> FEATURE:
<221> NAME/KEY: protein_bind
<223> OTHER INFORMATION: consensus DNA sequence for the binding of NfkB
    p50-p65 heterodimer,

```
-continued

<400> SEQUENCE: 1 gggactttc                                                                                   9

<210> SEQ ID NO 2
<211> LENGTH: 28
<212> TYPE: PRT
<213> ORGANISM: Unknown
<220> FEATURE:
<221> NAME/KEY: PEPTIDE
<223> OTHER INFORMATION: Cell-permeable NEMO (NF-(B essential modifier;
      also called IKK()-binding domain peptide

<400> SEQUENCE: 2

Asp Arg Gln Ile Lys Ile Trp Phe Gln Asn Arg Arg Met Lys Trp
                  5                  10                  15

Lys Lys Thr Ala Leu Asp Trp Ser Trp Leu Gln Thr Glu
             20                  25

<210> SEQ ID NO 3
<211> LENGTH: 17
<212> TYPE: PRT
<213> ORGANISM: Unknown
<220> FEATURE:
<221> NAME/KEY: PEPTIDE
<223> OTHER INFORMATION: Control peptide for cell-permeable NEMO

<400> SEQUENCE: 3

Asp Arg Gln Ile Lys Ile Trp Phe Gln Asn Arg Arg Met Lys Trp
                  5                  10                  15

Lys Lys

<210> SEQ ID NO 4
<211> LENGTH: 45
<212> TYPE: DNA
<213> ORGANISM: Human immunodeficiency virus-1
<220> FEATURE:
<221> NAME/KEY: gene
<223> OTHER INFORMATION: NF-_B oligonucleotide from human
      immunodeficiency virus-1 long terminal repeat

<400> SEQUENCE: 4
ttgttacaag ggactttccg ctggggactt tccagggagg cgtgg                                          45
```